United States Patent
Shah et al.

(10) Patent No.: US 11,259,842 B2
(45) Date of Patent: Mar. 1, 2022

(54) NEEDLE FOR TRANSCUTANEOUS ANALYTE SENSOR DELIVERY

(71) Applicant: DexCom, Inc., San Diego, CA (US)

(72) Inventors: Neel Shah, San Diego, CA (US); Jennifer Blackwell, San Diego, CA (US); Jonathan Hughes, Carlsbad, CA (US); Ted Tang Lee, San Diego, CA (US); Peter C. Simpson, Cardiff, CA (US); Shanger Wang, Castro Valley, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 15/160,516

(22) Filed: May 20, 2016

(65) Prior Publication Data
US 2016/0338733 A1    Nov. 24, 2016

Related U.S. Application Data

(60) Provisional application No. 62/244,520, filed on Oct. 21, 2015, provisional application No. 62/165,837, filed on May 22, 2015.

(51) Int. Cl.
*A61B 5/145* (2006.01)
*A61B 17/34* (2006.01)
(Continued)

(52) U.S. Cl.
CPC ...... *A61B 17/3468* (2013.01); *A61B 5/14503* (2013.01); *A61B 5/14532* (2013.01);
(Continued)

(58) Field of Classification Search
CPC ............ A61B 17/3468; A61B 5/14503; A61B 5/14532; A61B 5/14865; A61B 2017/3456; A61B 2560/063; A61M 5/3286
(Continued)

(56) References Cited

U.S. PATENT DOCUMENTS 2,697,438 A * 12/1954 Hickey ............... A61M 5/3286
604/274
2,717,599 A *  9/1955 Huber ................. A61M 5/3286
604/274
(Continued)

FOREIGN PATENT DOCUMENTS

WO    WO 2009-024522    2/2009
WO    WO 2012-118872    9/2012

OTHER PUBLICATIONS

International Preliminary Report on Patentability for Application No. PCT/US2016/033612 dated Dec. 7, 2017, 11 pages.
(Continued)

*Primary Examiner* — Navin Natnithithadha
(74) *Attorney, Agent, or Firm* — Snell & Wilmer LLP

(57) ABSTRACT

The present disclosure relates to a needle including a wall structure, a cutting edge and a blunt contour. The needle advantageously can be used to deliver a sensor (such as a glucose or other analyte sensor) through an outer skin layer and into a sensor depth in a less invasive way than prior art needles. The size of the cutting edge is balanced against a portion of the distal wall structure that has blunt contours. Thus, the needle is capable of cutting the more durable outer skin layer (first phase) and then progressively stretching open the cut for further advancement into the subcutaneous layer (second phase). When the needle is sufficiently advanced, it is retracted leaving the sensor in a desired position. Early testing has shown a reduction of "dip and recover" from glucose sensors delivered using the needle.

20 Claims, 26 Drawing Sheets

(51) Int. Cl.
*A61B 5/1486* (2006.01)
*A61M 5/32* (2006.01)

(52) U.S. Cl.
CPC ....... *A61B 5/14865* (2013.01); *A61M 5/3286* (2013.01); *A61B 2017/3456* (2013.01); *A61B 2560/063* (2013.01)

(58) Field of Classification Search
USPC .......................................... 600/309, 345–366
See application file for complete search history.

(56) References Cited

U.S. PATENT DOCUMENTS

| | | | | |
|---|---|---|---|---|
| 2,751,907 | A * | 6/1956 | Hickey | A61M 37/0069 604/60 |
| 3,071,135 | A * | 1/1963 | Baldwin | A61M 5/3286 604/274 |
| 3,308,822 | A * | 3/1967 | De Luca | A61M 5/3286 604/274 |
| 3,448,740 | A * | 6/1969 | Figge | A61M 5/3286 604/274 |
| 3,924,617 | A * | 12/1975 | Ferro | A61M 1/008 604/411 |
| 4,808,170 | A * | 2/1989 | Thornton | A61M 5/158 604/274 |
| 4,889,529 | A * | 12/1989 | Haindl | A61M 5/158 604/274 |
| 5,403,296 | A * | 4/1995 | Mohring | A61M 25/065 604/158 |
| 5,456,675 | A * | 10/1995 | Wolbring | A61M 5/158 604/170.03 |
| 5,515,817 | A | 5/1996 | Nurmi et al. | |
| 5,515,871 | A | 5/1996 | Bittner et al. | |
| 5,568,806 | A * | 10/1996 | Cheney, II | A61B 5/14532 600/373 |
| 5,968,022 | A * | 10/1999 | Saito | B24B 19/16 604/264 |
| 7,458,142 | B2 * | 12/2008 | Haindl | A61M 5/3286 128/897 |
| 7,645,268 | B2 * | 1/2010 | Mickley | A61M 5/3286 604/274 |
| 7,780,973 | B2 * | 8/2010 | Freeman | A61L 31/148 424/423 |
| 8,002,752 | B2 * | 8/2011 | Yodfat | A61B 5/6849 604/198 |
| 8,328,772 | B2 * | 12/2012 | Kinast | A61M 5/3286 604/274 |
| 8,628,500 | B2 * | 1/2014 | Yodfat | A61B 5/6849 604/198 |
| 8,696,570 | B2 * | 4/2014 | Yodfat | A61B 5/14503 600/309 |
| 8,715,232 | B2 * | 5/2014 | Yodfat | A61B 5/6849 604/112 |
| 8,764,657 | B2 * | 7/2014 | Curry | A61B 5/15194 600/309 |
| 8,828,201 | B2 | 9/2014 | Simpson et al. | |
| 8,954,128 | B2 | 2/2015 | Boock et al. | |
| 9,451,912 | B2 | 9/2016 | Atsushi et al. | |
| 9,597,461 | B2 * | 3/2017 | Aasmul | A61M 5/3286 |
| 9,615,779 | B2 | 4/2017 | Pryor | |
| 9,687,183 | B2 * | 6/2017 | Donnay | A61B 5/15194 |
| 9,782,536 | B2 | 10/2017 | Skutnik et al. | |
| 9,931,065 | B2 | 4/2018 | Pryor | |
| 9,937,296 | B2 | 4/2018 | Pryor | |
| 10,010,280 | B2 * | 7/2018 | Donnay | A61B 5/14503 |
| 2005/0131386 | A1 * | 6/2005 | Freeman | A61L 31/148 604/522 |
| 2005/0215977 | A1 * | 9/2005 | Uschold | A61M 5/3286 604/506 |
| 2008/0319414 | A1 * | 12/2008 | Yodfat | A61B 5/6849 604/506 |
| 2008/0319416 | A1 * | 12/2008 | Yodfat | A61B 5/6849 604/513 |
| 2010/0106088 | A1 * | 4/2010 | Yodfat | A61B 5/6849 604/112 |
| 2010/0137695 | A1 * | 6/2010 | Yodfat | A61B 5/6849 600/345 |
| 2010/0217105 | A1 * | 8/2010 | Yodfat | A61B 5/14503 600/365 |
| 2010/0249558 | A1 * | 9/2010 | Yodfat | A61M 5/14248 600/345 |
| 2010/0256593 | A1 * | 10/2010 | Yodfat | A61M 5/14248 604/504 |
| 2010/0268043 | A1 * | 10/2010 | Yodfat | A61B 5/0002 600/345 |
| 2011/0077490 | A1 | 3/2011 | Simpson et al. | |
| 2011/0288390 | A1 * | 11/2011 | Yodfat | A61B 5/6849 600/365 |
| 2011/0288574 | A1 * | 11/2011 | Curry | A61B 5/15194 606/185 |
| 2011/0313357 | A1 * | 12/2011 | Skutnik | A61M 5/14248 604/151 |
| 2011/0319729 | A1 * | 12/2011 | Donnay | A61B 5/15194 600/309 |
| 2012/0190941 | A1 * | 7/2012 | Donnay | A61B 5/15194 600/309 |
| 2012/0190942 | A1 * | 7/2012 | Donnay | A61B 5/15194 600/309 |
| 2012/0190943 | A1 * | 7/2012 | Donnay | A61B 5/15194 600/309 |
| 2012/0190951 | A1 * | 7/2012 | Curry | A61B 5/15194 600/345 |
| 2012/0197098 | A1 * | 8/2012 | Donnay | A61B 5/15194 600/345 |
| 2012/0197222 | A1 * | 8/2012 | Donnay | A61B 5/15194 604/318 |
| 2012/0259185 | A1 * | 10/2012 | Yodfat | A61M 5/14244 600/309 |
| 2012/0303043 | A1 * | 11/2012 | Donnay | A61B 5/6849 606/129 |
| 2013/0267811 | A1 | 10/2013 | Pryor et al. | |
| 2015/0051457 | A1 * | 2/2015 | Matsumoto | A61B 5/1495 600/309 |
| 2015/0328370 | A1 * | 11/2015 | Petisce | A61L 31/10 600/365 |
| 2016/0338628 | A1 * | 11/2016 | Shah | A61B 17/3468 |
| 2016/0338733 | A1 * | 11/2016 | Shah | A61B 17/3468 |
| 2016/0338734 | A1 * | 11/2016 | Shah | A61B 17/3468 |

OTHER PUBLICATIONS

International Search Report and Written Opinion for Application No. PCT/US2016/033612 dated Sep. 2, 2016, 13 pages.
Communication Under Rule No. 71(3) for EP Application No. 16730084.7 dated Sep. 3, 2021, 67 pages.

* cited by examiner

| Test Sample | D (µm) | L (µm) | Volume (µm^2) | % Reduction |
|---|---|---|---|---|
| Conventional | 47.5 | 672 | 396940 | 48.76 (FIG. 11) |
| Inventive | 34.3 | 672 | 203374 | |
| Conventional | 81 | 575 | 987657 | 69.14 (FIG.10) |
| Inventive | 45 | 575 | 304832 | |

FIG. 12

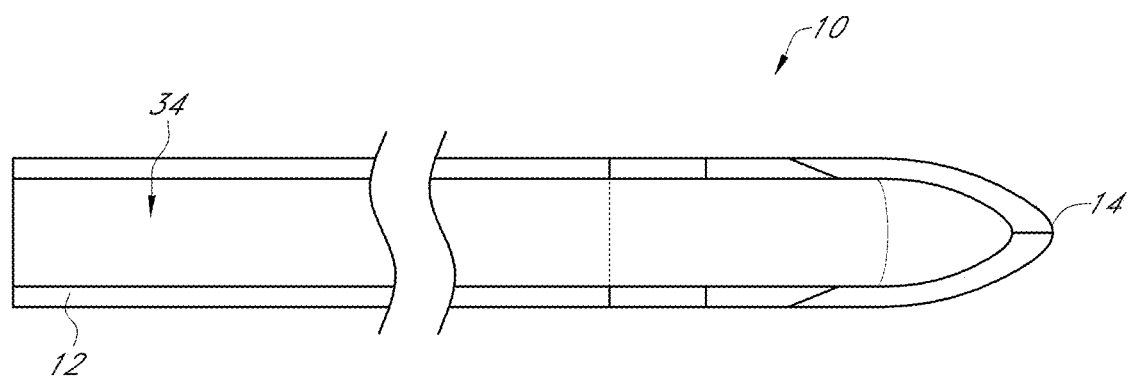
FIG. 21
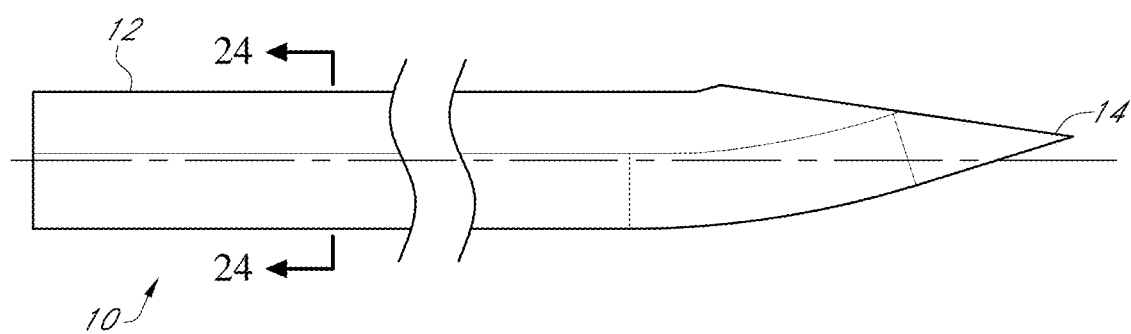
FIG. 22
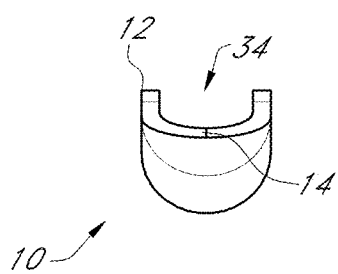 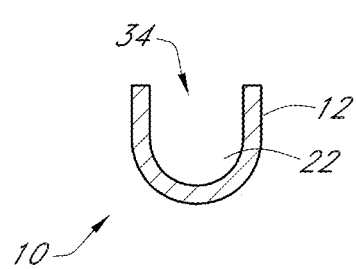
FIG. 23              FIG. 24

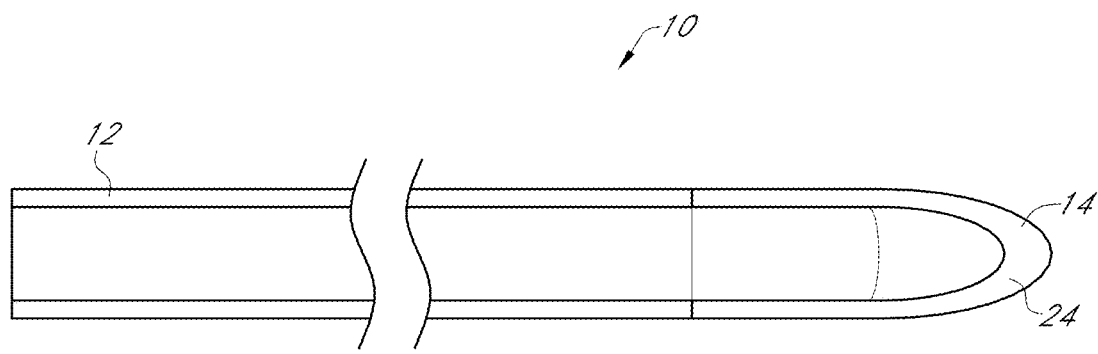
FIG. 41
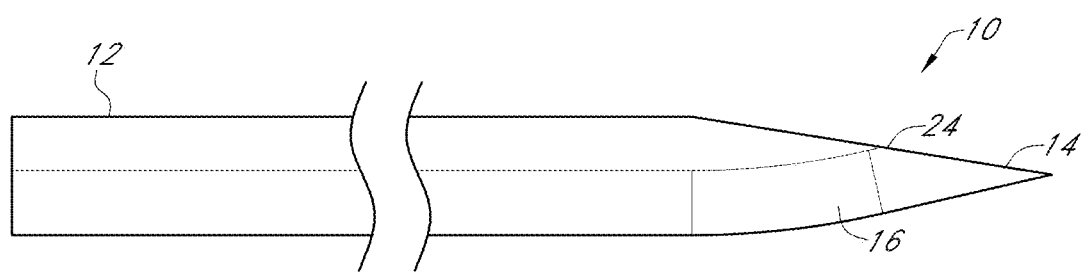
FIG. 42
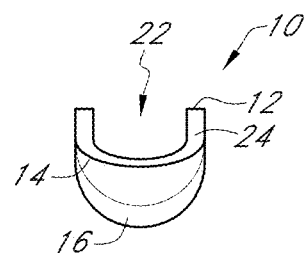 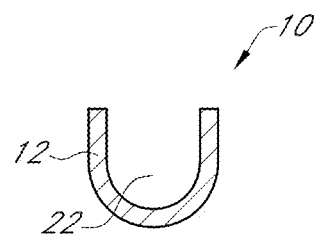
FIG. 43          FIG. 44

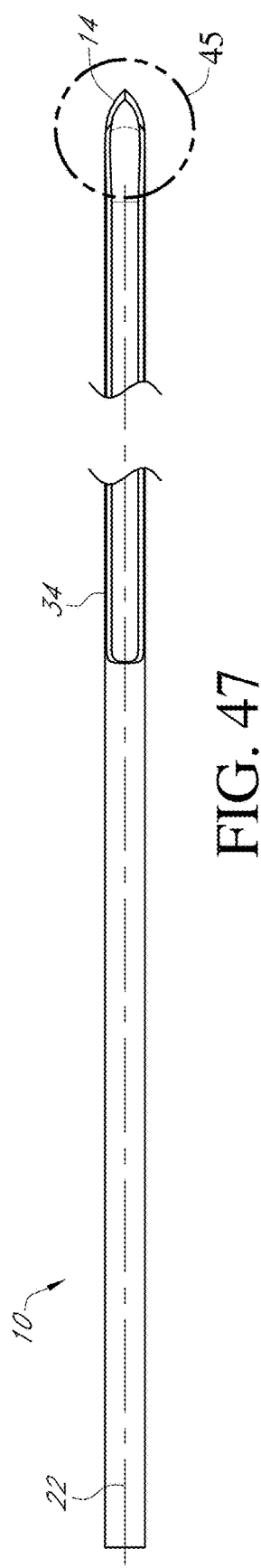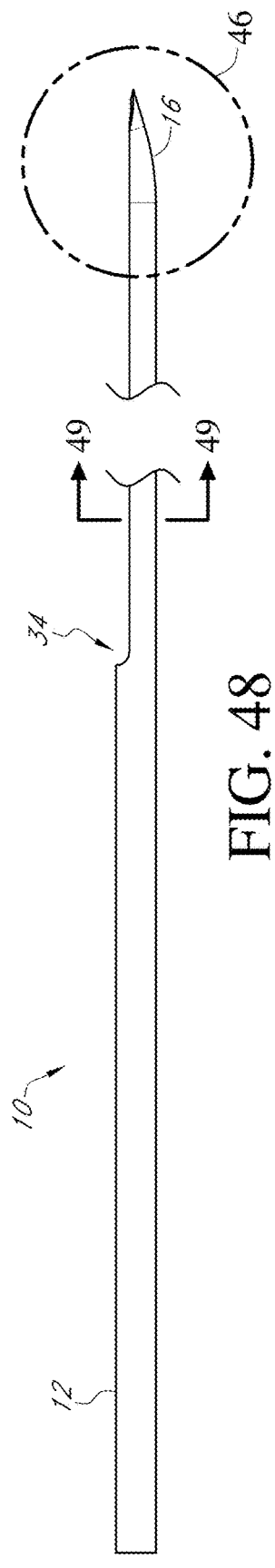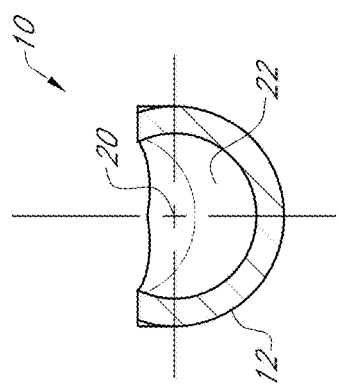
FIG. 47
FIG. 48
FIG. 49

|  | Mean | Std Dev | Min | Max | N | Median |
|---|---|---|---|---|---|---|
| Manual Conventional | 31872 | 5825 | 23566 | 50574 | 32 | 30724 |
| Manual Dual Bevel | 14564 | 4575 | 6167 | 30039 | 35 | 13416 |
| Manual Single Bevel 17° | 11459 | 2677 | 7081 | 18989 | 24 | 11398 |
| Auto Conventional | 43103 | 11058 | 23449 | 66947 | 18 | 42258 |
| Auto Single Bevel 17° | 17588 | 2239 | 12171 | 20576 | 10 | 17860 |
| Auto Single Bevel 13° | 16846 | 3364 | 12547 | 23835 | 10 | 16083 |

FIG. 51

NEEDLE FOR TRANSCUTANEOUS ANALYTE SENSOR DELIVERY

INCORPORATION BY REFERENCE TO PRIORITY APPLICATIONS

Any and all priority claims identified in the Application Data Sheet, or any correction thereto, are hereby incorporated by reference under 37 CFR 1.57. This application claims priority to U.S. Provisional Application No. 62/165,837, filed May 22, 2015, and U.S. Provisional Application No. 62/244,520 filed Oct. 21, 2015. Each of the aforementioned applications is incorporated by reference herein in its entirety, and each is hereby expressly made a part of this specification.

FIELD

The present disclosure relates to a delivery device for a sensor, and in particular to a needle for transcutaneous analyte sensor delivery.

BACKGROUND

Physicians who understand a patient's glucose level can better adapt to various treatments, such as the administration of insulin, to the patient's needs. Most diabetic patients (and many healthcare institutions) use occasional finger sticks with test strips to measure patient glucose. Test strips, however, do not convey the same dynamic information (such as trend information) on the patient's glucose levels.

Continuous glucose monitors have the advantage of providing multiple measurements over short time periods with little additional labor and less pain. Continuous glucose monitors often use transcutaneous sensors—sensors positioned through the patient's skin—to accurately measure glucose values. For example, the transcutaneous sensors may dwell several layers deep in the patient's skin and are bathed in interstitial or other fluids. The sensors often include electrodes that are sensitive to glucose composition and yield fairly frequent (e.g., every few minutes) measurements.

Patients and physicians prefer the glucose sensors to be small to minimize invasiveness and discomfort. The glucose sensors therefore tend to be relatively fragile. At the same time, the patient's skin can be thick and difficult to penetrate. Physicians and patients therefore often use needles to pierce the skin to its appropriate layer and depth. The needle houses an electrode portion of the glucose sensor during insertion and is later withdrawn to leave the sensor at the appropriate position within the patient's skin.

As another example, DexCom, Inc. (applicant on the present application) owns U.S. Patent Application Publication No. 2011/0077490 which discloses a transcutaneous analyte sensor. The '490 publication discloses in its FIGS. 1 and 2A, for example, a transcutaneous sensor device that includes a tissue piercing element positioned over a sensor body. The piercing element has a conical shape that enables piercing of the skin for advancement of the sensor body. The '490 publication also discloses, in FIG. 2B, a distal tip that is beveled at an angle from about 5° to 60°. The '490 publication also discloses, in FIGS. 2C-2H and 3D, tips with curved surfaces providing greater cutting surface area for smoother insertion.

SUMMARY

Despite the improvements disclosed in the '490 publication, DexCom is continuously improving the delivery of its sensors. DexCom discloses herein another design of a needle for delivering sensors that balances invasiveness with other needs of the patient, physician and sensor.

The present disclosure in some embodiments relates to a needle including a wall structure, a cutting edge and a blunt contour. The needle advantageously can be used to deliver a sensor (such as a glucose or other analyte sensor) through an outer skin layer and into a sensor depth in an effective but less invasive way than prior art needles. The size of the cutting edge is balanced against a portion of the distal wall structure that has blunt contours. Thus, the needle is capable of cutting the more durable outer skin layer (first phase) and then progressively stretching open the cut for further advancement into the subcutaneous layer (second phase). When the needle is sufficiently advanced, it is retracted away from the sensor leaving the sensor in a desired position. Early testing has shown a reduction of "dip and recover" from glucose sensors delivered using the needle.

A needle for delivering a sensor through an outer skin layer and into a sensor depth is disclosed. The needle includes a wall structure, at least one cutting edge and at least one blunt contour. The wall structure has a central axis, at least one cross dimension and defines at least one inner dimension. The inner dimension is sized to contain the sensor for delivery. The cutting edge is on the wall structure and is configured to pierce the outer skin layer. The blunt contour is also on the wall structure. It is configured to bluntly dissect tissue as the wall structure advances to the sensor depth. The projected area of the blunt contour, when viewed along the central axis of the wall structure, can occupy more than 50% or 60% of the cross dimension of the wall structure. The wall structure is also configured for removal from the outer skin layer to leave the sensor at the sensor depth.

Beveled edges may be defined on the wall structure. The cutting edge may be formed on less than 50% of the beveled edge. Also, the cutting edge (from a view along the central axis) may be spaced closer to the central axis than an adjacent outer edge of the blunt contour. And, the central axis may pass through the blunt contour. The remaining portion of the beveled edge may be smoothed rather than sharpened.

The blunt contour in one implementation is at least ⅔ of an area centered on the central axis and circumscribing an outer edge of the blunt contour. The area may be, for example, a circular area having a diameter matching a diameter of the wall structure.

The cutting edge may form less than 40% of the beveled edge. The blunt contour may be sufficiently large in proportion to the cutting edge to reduce wound volume by at least 15% to 69% or 70%. Observed incidences of dip and recover in human populations are, based on early porcine testing, expected to drop to less than 5% or even less than 1% of the population.

The needle may be detachable from the sensor to leave the sensor at the sensor depth.

In one implementation, the wall structure of the needle has a cylindrical shape. Also, the cutting edge may be configured to be sufficiently sharp and large to cut through the outer skin layer without buckling of the wall structure.

The beveled edges may be at a range of angles. For example the beveled edges may be angled at least 7 to 10 degrees. For example, the wall structure may include a primary bevel that is angled 7 degrees. The needle may also include a secondary beveled edge that has two portions angled away from each other and the central axis.

The wall structure may further include a bend positioned proximal and subjacent to the primary bevel, the beveled edge or the cutting edge. The bend may be 17 degrees or up to 24 degrees. An inner dimension of the wall structure may be at least 0.0135 inches to afford clearance for the sensor diameter. An outer dimension of the wall structure may be at least 0.0180 inches. The inner dimension may be, for example, a diameter of an elongate cylindrical opening.

The elongate opening may be configured to retain the sensor until the wall structure reaches the sensor depth. At the same time the elongate opening may be configured to allow the sensor to slide freely therein. The elongate opening may be of sufficient length to retain the sensor in a recessed position relative to the distal tip of the wall structure.

In another embodiment, the wall structure may define a longitudinal slit connected in communication with the inner dimension. Also, the wall structure may define an elongate opening. The inner dimension is a diameter of the elongate opening. The longitudinal slit is in communication with the elongate opening. And, the elongate opening is sized to retain the sensor until the wall structure reaches the sensor depth. The longitudinal slit may be sized to allow passage of a width of the sensor therethrough. And the elongate opening may be a cylindrical opening. The elongate opening and longitudinal slit may extend entirely through a distal edge of the wall structure to form a C-shape.

In another aspect, the elongate opening may form a window in the wall structure. This window can, for example, allow passage therethrough of connector wires for the sensor.

Other systems, methods, features and/or advantages will become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

FIG. 12 is a table of test results comparing geometries of needle holes formed using a needle similar to the ones shown in FIGS. 1-8 and the needle shown in FIG. 9;

FIGS. 21-24 illustrate a needle of another embodiment with a U-shaped cross-section;

FIGS. 41-44 show a single bevel needle having a U-shaped cross-section;

FIGS. 45-49 show a single bevel needle having a C-shaped cross-section;

FIG. 51 shows a table of cut area test results for needles;

DETAILED DESCRIPTION

Figure 1:
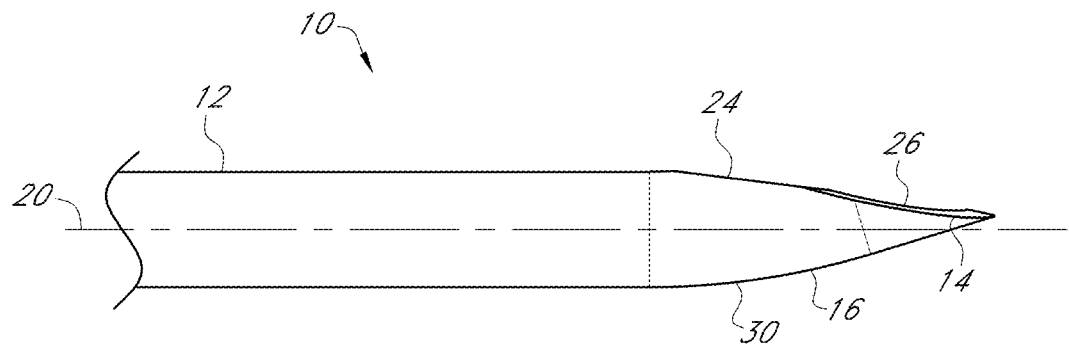
FIG. 1 shows an elevation view of a needle of one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

It was determined that that continuous glucose monitoring (CGM) systems exhibit at times a characteristic called "dip and recover." The dip and recover phenomenon occurs after initial placement of the sensor—the signal from that sensor dips from expected levels and then later recovers to normal behavior. One drawback of an occurrence of a dip and recover event is lost time and lost data in what would otherwise have been a robust, continuous measure of glucose containing dynamic information desired by physicians.

Generally, the dip and recover phenomenon was reduced by developing a needle and sensor insertion system designed specifically to minimize tissue trauma during sensor insertion. Minimization of tissue trauma may also advantageously reduce the likelihood of a dip and recover event during sensor use. The needle is designed with a tip that pierces the skin, but continues with blunt dissection through the subcutaneous tissue to the depth of sensor placement. Blunt dissection occurs without substantial trauma (breakage of cells) during subcutaneous penetration. Subsequently, the needle is withdrawn, leaving behind the sensor in the subcutaneous tissue with minimal trauma to the patient. Although the needle and sensor insertion does not always completely eliminate dip and recover, a substantial reduction in the likelihood of the dip and recover failure mode on day one of sensor implantation was observed.

In some embodiments, the needle is specifically designed with three sometimes competing design criteria: 1) to pierce the skin, 2) to push through, but not pierce, the cells and tissues within the subcutaneous space, and 3) to be removable from the host without causing discernible tissue trauma during the removal process. Needle removal leaves the sensor in place to function without substantial interference resulting from wound healing as seen in prior art devices. Other embodiments are also disclosed with configurations that help to mediate or address the dip and recover phenomena. It should be noted that although reduction of dip and recover occurrences to less than 5% or even 1% is desired, there are other advantages of the embodiments. Reduced wound trauma and increased comfort is generally desired from a healing and patient safety standpoint.

The needle designs described herein may also extend the functional life of the sensor. Typically, after sensor insertion, a foreign body response from the body is triggered which typically eventually results in encapsulation of the inserted object (e.g., an inserted sensor) and biofouling of certain components (e.g., the membrane) of the inserted object. As more and more amounts of biomaterial (e.g., proteins) accumulates through encapsulation and/or biofouling, diffusion of the analyte being measured (e.g., glucose) from interstitial fluid through the sensor's membrane becomes reduced, less and less amounts of analyte are able diffuse through the membrane, thereby reducing the sensor's functionality.

While not wishing to be bound by theory, it is believed that with a needle design that minimizes tissue trauma during the sensor insertion process, it may be possible to achieve a delay in the foreign body response and/or a foreign body response that is less severe, as compared to one with a conventional needle. In turn, by achieving a delay and/or a reduced severity in the foreign body response, the life of the sensor can be extended, as compared to sensors inserted with a conventional needle.

With somewhat more specificity for some method embodiments, the needle is designed to operate in three phases.

In phase one, the cutting edge (a first zone) of the needle is designed to cut through the tough part of the skin/dermis only, not into the subcutaneous tissue. The needle includes a cutting-edge size and shape design, which, in combination with an insertion force provided by the system, allows the tip to pierce the skin to a predetermined depth, while minimizing further cutting into the soft tissue in the subcutaneous layer.

In phase two, a portion of the needle is designed with a non-cutting or blunt surface (a second zone), which pushes through the subcutaneous tissue, minimizing trauma to, or minimizing the cutting of, surrounding soft tissue. The system is configured in such a way that during the second phase of needle insertion, post skin-piercing, the blunt/non-cutting portion of the needle advances through the subcutaneous tissue, while the cutting surface of the needle is substantially prevented from cutting through subcutaneous tissue. The first sharp zone therefore creates the hole with the initial penetration and the next layer of tissue is dilated by the second, non-cutting zone with little further trauma.

In phase three, the needle is retracted to leave the sensor in the patient. The needle design may allow the sensor to be retained in the needle during two phases of needle insertion: cutting and blunt pushing. At the same time, the needle may still be easily released (without damaging sensor), leaving the sensor in the tissue when needle is retracted. For example, the needle may be designed such that sensor release is independent of the piercing function by spacing or recessing the sensor from the distal cutting tip of the needle.

The above—and below—described aspects and embodiments, depending upon their configuration, can have advantages over prior art needle designs—including, for example, reduction in the occurrence of "dip and recover" events. Prior art needle designs have extended cutting surfaces that continue cutting through the subcutaneous tissue after piercing the relatively thick outer dermis layer. This is believed to cause tissue trauma (such as breakage of cells) around the sensor. Without being bound by theory, it is believed that this trauma interferes with sensor function. In particular, it is believed that cutting through the subcutaneous tissue with the same cutting surface used to pierce the skin can cause trauma to the sensor insertion site, which in turn can affect sensor function. As observed by signal suppression, this typically occurs during the first 2-24 hours after needle insertion.

Prior art sensor deployment needles also include a centrally located lumen to allow the sensor to extend out of one end of the needle. A drawback of this design is that the cutting surfaces typically need to extend around the centrally located lumen to protect the sensor. Again, as described above, these cutting surfaces may cause excess damage at the insertion site.

As shown in FIG. 1, a needle 10 includes a wall structure 12, a cutting edge 14 and a blunt contour 16. The needle 10 advantageously can be used to deliver a sensor 18 (such as an analyte sensor, for example, a glucose sensor) through an outer skin layer and into a sensor depth in a less invasive way than when performed by prior art needles. In the needle design, the size of the cutting edge 14 is balanced against a portion of the distal wall structure 12 that has blunt contours 16. Thus, the needle 10 is capable of cutting the more durable outer skin layer (first phase) and then progressively widening open the cut for further advancement into the subcutaneous layer (second phase) with minimal tissue trauma. When the needle is sufficiently advanced with the sensor therein, the needle and the sensor are then detached, and the needle is retracted leaving the sensor 18 in a desired position. Early testing has shown a reduction of "dip and recover" incidents (and reduction in average duration of an incident) with glucose sensors delivered using the needles described herein.

The term "needle" as used herein should be construed to cover any delivery device that can contain the sensor 18 for delivery to the appropriate depth. The "needle" can have any of a variety of shapes with regard to its wall structure 12. For example, the wall shape can be cylindrical with a circular cross-section or can have a V-shaped, square or rectangular, or even some irregular, cross-section. The wall shape also need not be an extruded shape with the same cross-section along its axis. For example, the wall shape may start as a cylindrical tube with a circular cross-section at a proximal end and then change to a V-shape (in cross section) as it approaches the distal end. The wall shape may also have defined along its length slots or various openings—such as a slot that gives it a C-shape in cross-section. (The open cross-section of the C or V-shapes affords clearance for attachment of wiring, for example.)

Generally, however, the wall structure 12 defines some inner (relative to some outer surface of the wall) dimension (width or diameter for example) that supports or contains the sensor 18 for subcutaneous delivery. For example, in a V-shaped cross-section, the inner part of the V near its base has a diameter that is occupied by the sensor lodged between the two inner wall surfaces. Thus, the "dimension" is defined by the position that the sensor occupies (or would occupy) during delivery in or on the needle wall structure 12. The term "needle" also covers other devices (with different names) that share similar wall structures and functions (e.g., delivery of an implantable device), such as, for example, a tube, channel, cannula, catheter or blunt dilator with a recess or opening for deployment of an implantable device (e.g., a sensor).

The wall structure 12 of the needle 10 has, in the embodiment of FIG. 1, a tubular shape defining a central opening 22 with a central axis 20. The wall structure 12 is formed from a tube by bending, machining and polishing as shown generally by FIGS. 3-5. The proximal end of the wall structure 12 retains its stock tubular shape and has, for example, an outside diameter of 0.018 plus 0.001 or minus 0.0005 inches. Preferably, the inside diameter is an inner dimension sized to contain a cross-section of the sensor 18 for its delivery. The sensor 18 has a smaller cross sectional diameter than the diameter of the central opening 22. The size and shape of the central opening 22 may vary though according to the size and shape of the sensor 18 being delivered. As noted above, the needle 10 may have a wall structure 12 with a shape that varies axially and in cross-section. For example, the wall structure cross-section could have a rectangular, C-shape or V-shape, as will be discussed in more detail below.

In some embodiments, the outer diameter of the wall structure 12 at the proximal end, for example, may be about 0.0135 plus 0.001 or minus 0.0002 inches. The outer diameter and thickness of the wall structure 12 reflects a balance of columnar stiffness and minimization of the wound size for clearance of the needle through the patient's skin. In certain embodiments, the diameter of the wall structure 12 is minimized, but not to the point where the needle 10 is susceptible to buckling under the expected axial load from needle insertion.

In one aspect, the wall structure 12 has a length configured to retain and protect the sensor 16. In the case of one type of subcutaneously delivered glucose sensor, for example, the wall structure 12 has a length of about 2.31±0.02 inches.

The strength of the wall structure 12 (e.g., column strength) is determined in part by its material composition. A range of materials can be used, for example, steel (e.g., stainless steel), ceramics, titanium, tantalum, nickel, nickel-titanium, iridium, silver, palladium, platinum-iridium, iridium, ceramics, composites, and combinations or alloys thereof, and/or the like. Polymers that may be used include, but are not limited to, polycarbonate, polymethacrylic acid, ethylene vinyl acetate, polyesters, fluoropolymers including polytetrafluorethylene (TEFLON®), polyethylene, polypropylene, high density polyethylene, nylons, polyethylene terephthalate, and polyesters, combinations thereof, and the like. Stiffer materials like stainless steel (SS304 with a full hard temper) can store more deformation energy and have a higher modulus (190-203 GPa Young's modulus) and elastic limit (205-310 MPa) than many other materials and thus have good stiffness and resistance to buckling and permanent (plastic) deformation. This helps to keep the shape of the needle (and its ability to deliver the sensor) through penetration of the skin to the sensor depth. Also, steel has the advantage that it can be machined (formed, filed, ground, etc.) to create a sharper edge than many other materials. Further, steel tends to hold its edge well—the aforementioned modulus and energy storage capability keep the edge sharp through its use.

The insertion force and buckling strength of the needle 10 has been determined. The needle 10 is inserted at 45 degrees into 10N Syndaver at 1 in/min Peak insertion force was measured using a 10N load cell. Insertion forces were measured for 8 attempts at an average of 0.22b lbf with a minimum of 0.156 lbf and a maximum of 0.298 lbf and a standard deviation of 0.0505. Insertion forces were also measured for conventional needles and averaged 0.191 lbf with a range of 0.163 lbf and 0.237 lbf and a standard deviation of 0.0239.

Buckling strength was tested by compressing the needle 10 against a non-pierceable (metal plate) and measuring the axial force required to buckle the needle using the 10N load cell. The buckling strength of the needle 10 was (for 8 samples) 2.505 lbf on average with a minimum of 2.185 lbf and a maximum of 2.280 lbf and a standard deviation of 0.2189. For conventional needles, 2.458 lbf on average with a minimum of 2.158 lbf and a maximum of 2.755 lbf was measured.

The ratios of buckling strength as a ratio to insertion force ranged from about 7.3 to 14.6 times the insertion force. Thus, the needle 10 is capable of withstanding buckling even with presentation of some relatively high percentage of blunt contour for dilation of the skin opening.

The "central axis" is a reference point for an amount and positioning of the cutting edge 14 and blunt contours relative to the proximal portion of the sensor 16 (or where the sensor would be if it were within the needle 10). For example, the central axis of the wall structure 12 in the implementation of FIG. 1 is defined by the unbent proximal end of the wall structure. Namely, the center, elongate axis of the proximal unbent tube of the wall structure—shown by the intermittently dashed line—is the central axis 20.

The central axis 20 is not limited to a linear shape. Generally, the central axis will be defined by a line through a series of points wherein the points are the centroids of a series of cross-sectional slices of the proximal end of the sensor 18. Thus, as the path of the sensor 18 bends or curves, the central axis 20 will follow. (The "centroid" is an average position of all of the points in a shape. For a cylindrical sensor it is the center of the circular cross-section. However, the sensor need not have any particular cross-sectional shape to define a central axis—even an irregular cross-sectional shape has a centroid.) Generally, then, the central axis defines a central location of the composite pathway of the sensor 18 proximal the edges and blunt contours as a reference point for the positioning of the edges and blunt contours 14, 16.

The central opening 22 is an opening in the center defined by a closed boundary wall structure—such as the one defined by the tubular portion of the needle 10 wall structure 12 in FIG. 1. The central opening 22 is an opening that is configured to receive (through sizing, finishing, etc.) the major dimensions (e.g., diameter or width) of the sensor 18 to be delivered.

Figure 6:
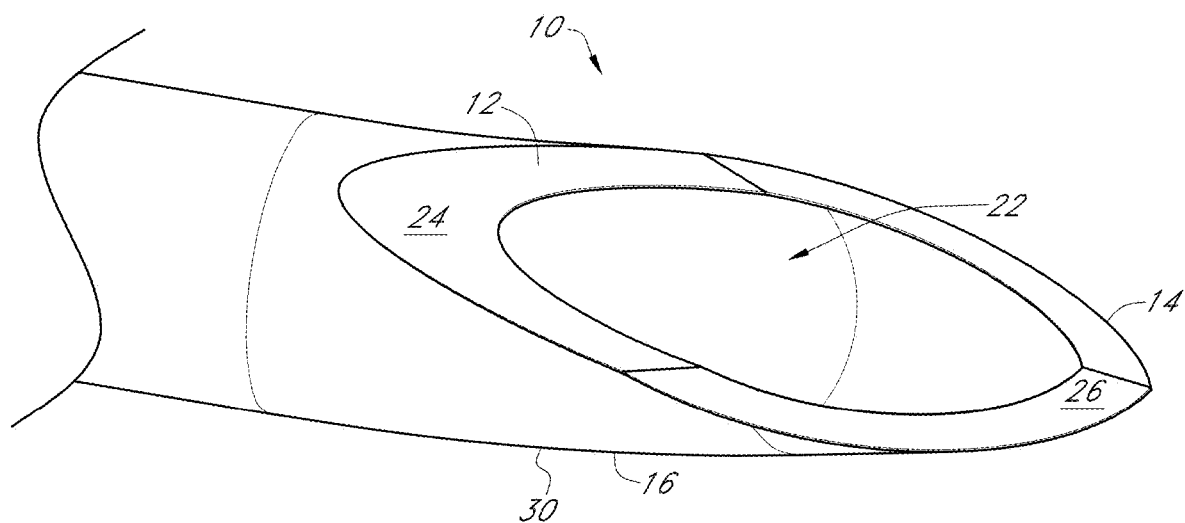
FIG. 6 shows an enlarged perspective view of the bevels of FIGS. 4-5.

Referring back to FIGS. 1, 2 and 6, the distal end of the wall structure 12 has formed thereon the cutting edge 14 and blunt contours 16. The blunt contours 16 may include a bend 30 in the wall structure 12 of the needle 10. The bend 30 is formed in the tubing used to create the wall structure 12, as shown in FIG. 3, prior to application of the bevels and cutting edge 14. The bend angle can range from about 5 degrees, in increments of one degree, to about 30 degrees for the cutting edge 14 configurations with primary bevel angles ranging from 3 to 12 degrees and (optionally) secondary bevel angles of 8 to 24 degrees.

The bend may be any of a variety of angles depending on the desired angle of entry of the tip of the cutting edge. Preferably, the bevel angle of the cutting edge 14 is balanced to the amount of blunt contour 16 seen by the skin as it is penetrated. The amount of blunt contour and cutting edge "seen" by the skin for example is the projected area occupied by the blunt contour and cutting edge when viewed along the central axis 20. (This captures a measure of what proportion of the blunt and cutting edges impacts the skin as the needle is advanced along the central axis line.) The blunt surface area is the amount of area occupied by the blunt contours of the needle from this view and the cutting surface area is the amount of surface area positioned opposite the blunt contours starting with the cutting edge, again as viewed along the central axis 20.

Generally, a design with a greater bend (and a larger blunt contour area seen at the insertion site) is more advantageous for reducing wound size. However, the extent of the bend (and size of the blunt contour seen at the insertion site) is limited by the need for some aspect of the cutting edge 14 to be positioned to penetrate the skin surface and form a hole large enough for expansion of the hole without further tearing. Thus the bevel angle or other angle of the cutting edge 14 relative to the central axis balances the amount of bend 30's angle.

Lubricants or other materials may be added into the lumen of the needle 10 to facilitate sensor withdrawal. For example, silane, silicone, parylene or other material with a low coefficient of friction may be added to the luminal surface of the needle. Coating the lumen walls with lubricious fluid improves the ease of release of the sensor without damaging the sensor membrane or otherwise inhibiting sensor operation.

The cutting edge 14 may include several sharpened edges or portions thereof in composite or a single planar facet forming a single sharpened edge. In any case, the cutting edge 14 in the embodiment of FIGS. 1 and 2 is formed on a set of beveled surfaces.

Figure 2:
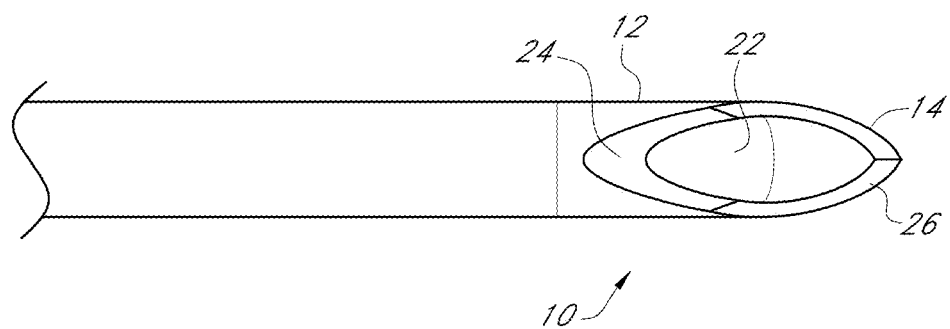
FIG. 2 shows a plan view of beveled surfaces of the needle of FIG. 1.
Figure 3:
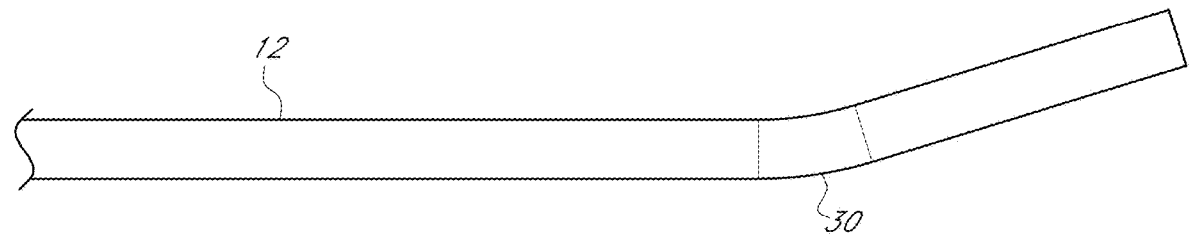
FIG. 3 shows an elevation view of tubing being bent to form a needle of another aspect.

The beveled surfaces may include a primary or proximal bevel 24 and a pair of secondary or distal bevels 26, as shown in FIG. 2. The primary bevel, as shown in FIG. 1, may extend at about a 7 degree angle relative to a line paralleling the central axis and extending from the outer surface of the wall structure 12 on the proximal, unbent end of the wall structure. The primary bevel could be at any of a variety of angles depending upon the desired proportion and orientation of forward facing cutting edge 14 and blunt contours 16. For example, the primary bevel 24 could be within a range of about 3 degrees to about 12 degrees, depending upon the amount of upstream bend in the wall structure 12.

Figure 4:
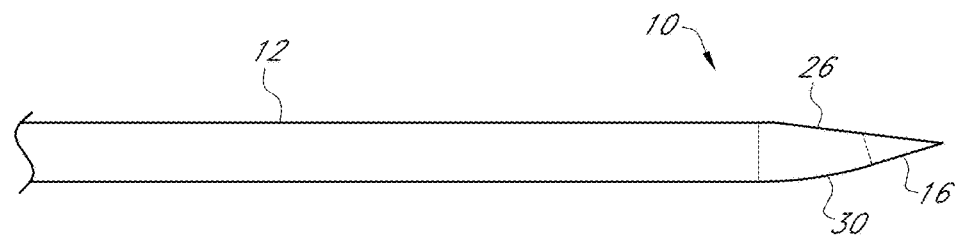
FIG. 4 shows an elevation view of the tubing of FIG. 3 with a primary bevel formed thereon.

In one implementation, the cutting edge 14 could be defined on a single, primary bevel 24 having an angle in the angle ranges described above, such as the angle shown in FIG. 4. (FIG. 4 is an intermediate stage in the process of manufacturing the needle 10 in FIG. 5, but represents where a single-bevel embodiment would stop for sharpening.) The distal edges of this primary bevel 24 could then be sharpened to form the cutting edge 14 sized in some desired proportion to polished edges and blunt contours to create the desired two-phase cutting and dilation that reduces invasiveness and dip and recover. (A more detailed description of how the blunt dissection and cutting surfaces are balanced in their proportions is described above and below in more detail.)

Figure 35:
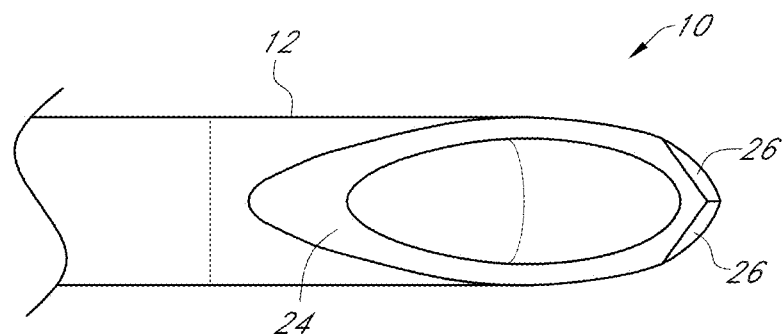
FIG. 35 shows another needle embodiment.
Figure 36:
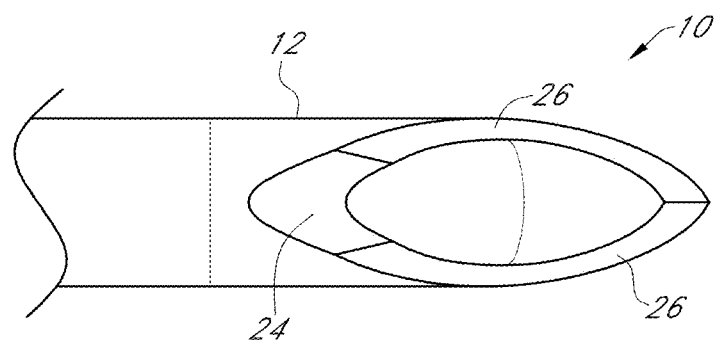
FIG. 36 shows another needle embodiment.

In certain embodiments, such as the one illustrated FIGS. 1, 2 and 5-8, two additional secondary or distal bevels 26 are formed on the distal tip of the wall structure 12 on the opposite side of the wall structure from the bend 30. (FIGS. 3 and 4 show the embodiment of FIG. 5 being formed from stock tubing.) Relative to the same reference point, the bevels 26 are angled at about 12.4 degrees, as shown in FIG. 1. The two distal bevels 26 may also define an angle between their proximal edges, as shown in FIGS. 35 and 36. FIG. 35 shows an angle between the proximal bevel edges of 120 degrees. FIG. 36 shows an angle between the proximal bevel edges of 20 degrees.

Figure 20:
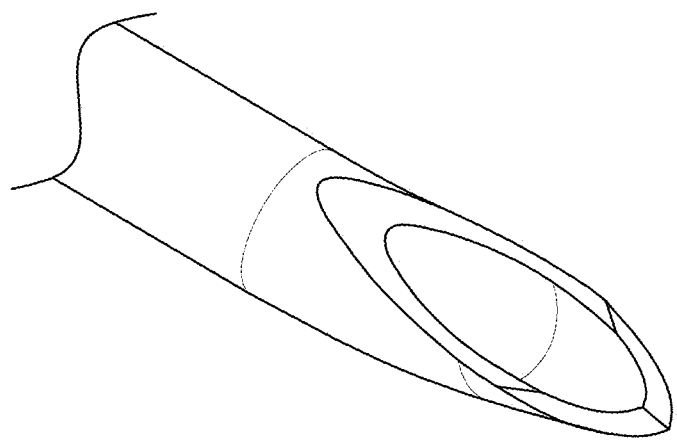
FIG. 20 is a needle of another embodiment.

The secondary bevels 26 may be varied in their angle from the outer surface line. However, a range of about 8 to 24 degrees balances the proportion of cutting edges 14 and blunt contours 16 for wound reduction. In yet another embodiment, shown in FIG. 20, the needle has a 17 degree bend 30, 7 degree primary bevel 24 and 16 degree secondary bevel 26.

In FIG. 2, the distance between the proximal most-tip of the beveled surfaces (along the central axis 20) to the distal-most tip of the beveled surfaces is 0.05±0.01 inches. The distance between the proximal most point of the secondary bevels 16 and the distal-most tip of the secondary bevels 16 is 0.03±0.006 inches.

Although the set of bevels 24, 26 form several axially oriented edges on the distal end of the wall structure 12, not all of those edges are necessarily sharpened. Instead, the cutting edge 14 is formed only on more distal portions of the secondary bevels 26. In particular, for example, on FIG. 7 a circle centered on the central axis is shown circumscribed about a bottom edge of the proximal wall structure 12 and extending over the bevels. In this implementation, only the portion of the bevels within the circle are sharpened. Those bevels outside the circle are rounded.

Figure 7:
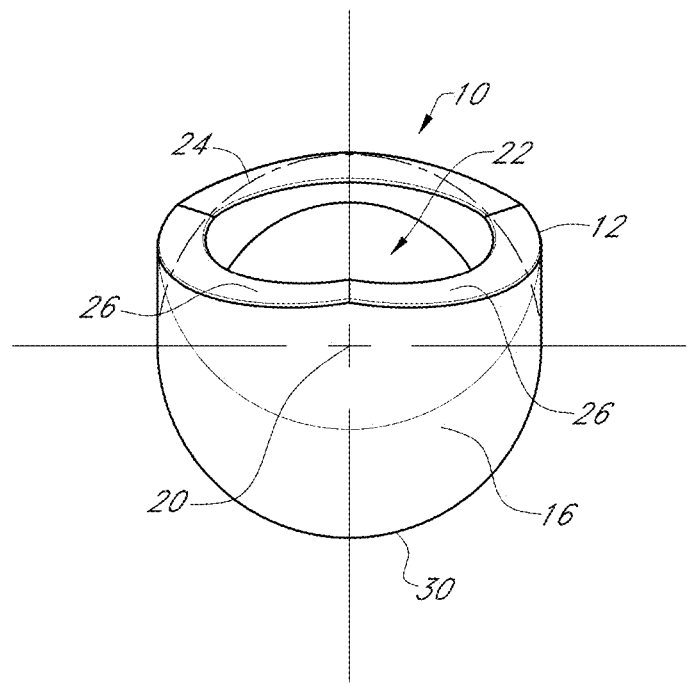
FIG. 7 shows a front elevational view (along a central axis) of the distal end of the bevels of FIGS. 3-5.

In the illustrated embodiment of FIG. 7, the circle has a diameter of 0.018 inches—the same diameter of the tube used to form the wall structure 12. The sharpened portion of the bevels 26 extends only to the edge of that circle as it maps onto the secondary bevels 26. Although having the advantage of matching up with the proximal cross-section of the wall structure 12, the sharpened portions can be expanded or reduced based on desired wound size, sensor characteristics, patient variation, etc.

The remainder of the edges of the bevels 24, 26 may be rounded into smoothed, non-cutting edges having about 2 to 3 thousandths of an inch radius or greater. For example, the heel and other edges of the primary bevel 24 may be blasted with media to smooth them. Blasting the heel of the bevel (the proximal, inner edge defining the central opening 22) may smooth it to reduce or eliminate coring, which occurs when the skin is picked up during needle 10 insertion (also sometimes referred to as "coring").

As shown in FIG. 7, in some embodiments, the needle design 10 balances the cutting edge 14 and blunt contours 16 to promote the two-phase cutting and dilation process of sensor 18 insertion. Various metrics can be used to define and describe the balance in the needle design between cutting edge 14 and blunt contour 15. For example, as shown in FIG. 7, in one embodiment, the cutting edge 14 only occupies about 60 degrees (33%) of the 180 degrees of the outer peripheral edge of the bevels 24, 26. Generally, the smaller the proportion of the edges of the bevels 24, 26 that are sharpened to the edges that are unsharpened, the smaller the initial wound before dilation. Variations are possible from 50% of the total edge being sharpened down to 20% in increments of 5%.

Figure 8:
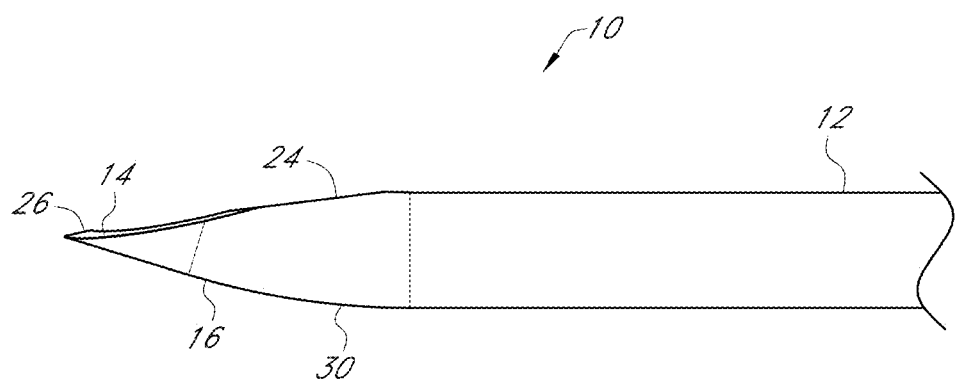
FIG. 8 shows a side elevational view of a needle of another aspect.
Figure 9:
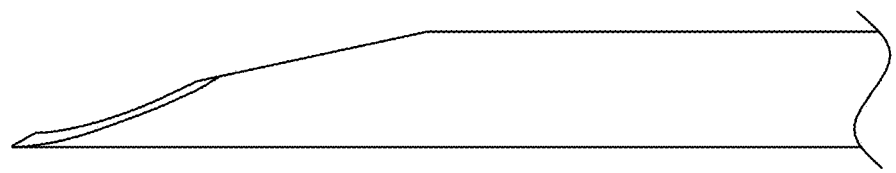
FIG. 9 shows a side elevational view of a conventional needle for delivering a sensor.

In one embodiment, the bend 30 advantageously repositions or offsets the leading point (and initial contacting cutting feature) of a conventional needle to the opposite side of the circular cross-section by 0.0112 inches, as shown by comparison of FIGS. 8 and 9. Thus, the offset of the point pushes it over (0.002 inches, as shown in FIG. 7) the central axis 20. For example, the point is about 62% of the way across the diameter to the opposite side of the circumscribed circle. In this manner, the central axis 20 (as it would for any offset of greater than 50% of the diameter or other relevant dimension associated with the position of the sensor) passes through the blunt contour 16 rather than above the cutting edge 14.

It should be noted, however, that an advantage of presenting a blunt contour 16 starts with any sized bend 30 (or other structure or modification) that moves the point and other cutting edges 14 within the outermost periphery of the circumscribed wall structure 12. Offsetting the cutting edge away from the outermost periphery and closer to (or past) the central axis than the adjacent outer edge by even 1% therefore results in some benefit of reduced invasiveness. Such positioning presents a blunt contour to the skin during insertion of the needle. Generally, the further the positioning across the dimension of the needle 10, the larger the proportion of the area presented to the skin that is made up by a blunt contour (versus cutting edge). For example, in some embodiments, the cutting edge can be repositioned across the dimension from about 5% to about 65% of the dimension in intervals of 5%. At the same time, some amount of cutting edge must be presented or no initial opening in the skin will be formed large enough to be dilated without tearing by the blunt dissection—hence the concept of "balance" between cutting and blunt dissection described above.

Although sometimes referred to as a diameter for the purposes of the round tubing used for wall structure 12 in the illustrated embodiments, the relevant "dimension" is any major dimension across the portion of the wall structure 12—or "cross dimension"—configured to hold the sensor.

Another metric that can be used to characterize the proportion of cutting edge 14 to blunt contour 16 is the projected area dedicated to blunt contours 16 projected along from a perspective viewed along the central axis 20. For example, as shown in a view along the central axis in FIG. 7, about ⅔ of the area of the circle circumscribing the outer edge of the rounded wall structure 12 is dedicated to blunt contour 16.

Figure 27:
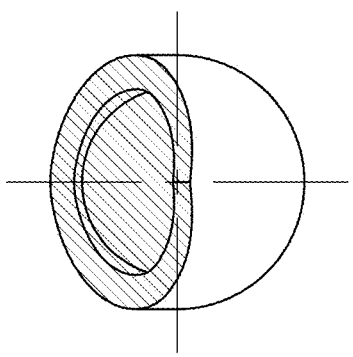
FIGS. 25-33 show schematics of additional needle embodiments.
Figure 30:
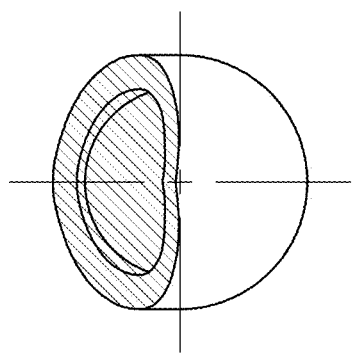
Figure 26:
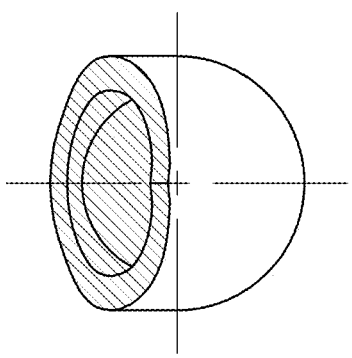
Figure 29:
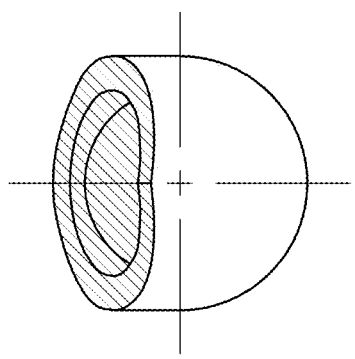
Figure 25:
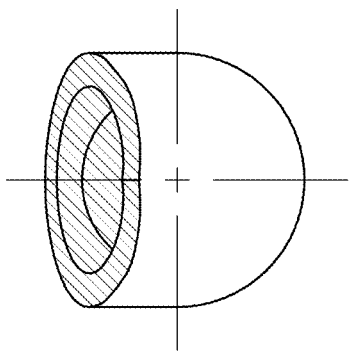
Figure 28:
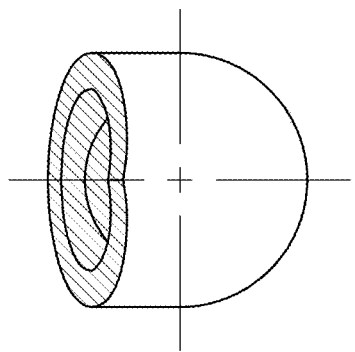
Figure 33:
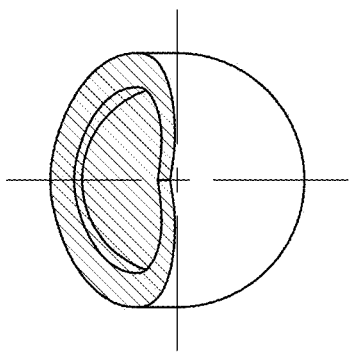
Figure 32:
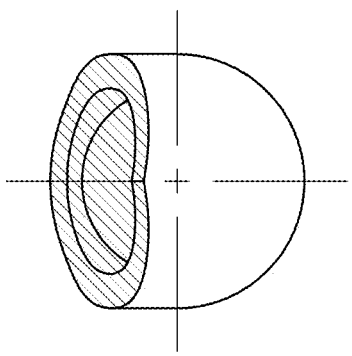
Figure 34:
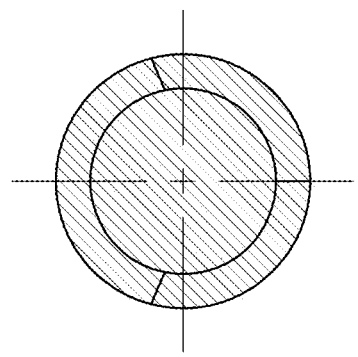
FIG. 34 shows a schematic of a conventional needle.
Figure 31:
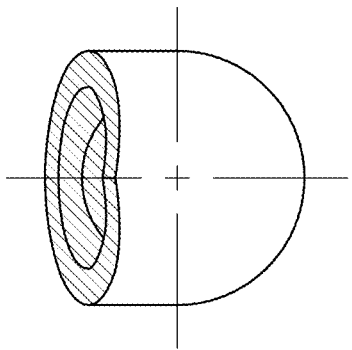

The various degrees of bend and bevel angles disclosed herein are not arbitrary. Rather, they impact wound size (and consequently dip-and-recover and other foreign body responses) and sensor deployment amongst other things. For example, FIGS. 25-33 and Table 1 below show variations in the bend angle and bevel angles and the impact on the ratio of blunt area (in grey) to cutting area (cross-hatched). Ratios run from as low as 0.85 for FIG. 27—where the blunt area is smaller than the cutting area—to as high as 2.74 times as much blunt area as cutting area for FIG. 31. Notably, there is an interplay between the bend angle and the bevel angles that determines the ultimate proportion. If a lower bend angle is used, then it restricts the amount of primary bevel angle before the blunt area drops dramatically and may not reduce wound formation. Eventually, the blunt area is so small as to approach that of the conventional needle shown in FIG. 34. Similarly, if a high bend angle is used, the cutting edge may not be sufficient to pierce the dermis layer during the initial cutting phase. The bend in the needle can also be limited by other constraints. If the bend is too severe, then the sensor could get stuck in the lumen of the needle and may not deploy. Or, the sensor may be damaged when it is deployed.

TABLE 1

| FIG. | Bend Angle (°) | Primary Bevel (°) | Secondary Bevel (°) | Cutting Surface Area (In^2) | Blunt Surface Area (In^2) | Ratio (Blunt SA/ Cutting SA) |
|---|---|---|---|---|---|---|
| 25 | 10 | 5 | 12 | 0.000096 | 0.000188 | 1.96 |
| 26 | 10 | 7 | 12 | 0.000122 | 0.000151 | 1.24 |
| 27 | 10 | 9 | 12 | 0.000143 | 0.000121 | 0.85 |
| 28 | 17 | 5 | 12 | 0.000079 | 0.000206 | 2.61 |
| 29 | 17 | 7 | 12 | 0.000104 | 0.000168 | 1.62 |
| 30 | 17 | 9 | 12 | 0.000126 | 0.000136 | 1.08 |
| 31 | 20 | 5 | 12 | 0.000076 | 0.000208 | 2.74 |
| 32 | 20 | 7 | 12 | 0.000101 | 0.000171 | 1.69 |
| 33 | 20 | 9 | 12 | 0.000124 | 0.000138 | 1.11 |

The relationship of the ratio (blunt surface area/cutting surface area) versus needle bend and primary bevel angle can be defined by an equation: Ratio (BSA/CSA)=$0.1895+0.2266*(\text{Bend Angle})-0.004952*(\text{Bend Angle})^2$ for a primary bevel angle of 5 degrees. The constants change with each of the primary bevel angle changes. Ratio=$0.171+0.1379*\text{Bend Angle}-0.003095*(\text{Bend Angle})^2$ for a primary bevel angle of 7 degrees. Ratio=$0.1329+0.09457*\text{Bend Angle}-0.002286*(\text{Bend Angle})^2$ for a primary bevel angle of 9 degrees. The changing constants can be determined via curve fit to the data above in Table 1 for different bevel angles.

Preliminary experiments have been conducted to evaluate the embodiments of FIGS. 1-7 with some favorable findings. Conventional needles and the above-disclosed needles were fed through clear silicone material and then removed. Testing was performed to track the needle's path and determine the cross-sectional area of the of the initial wound opening (at the surface). Dye was injected in the simulated wound to measure the volume. The needle tracks in FIG. 10 and FIG. 11 were created by the needle of FIG. 8 and the conventional needle of FIG. 9. Notably, the proximal ends of the needles are the same—with the same cylindrical wall shape and diameter. Only the distal end differs, starting at the bend 30 (e.g., as shown in FIG. 8) while the conventional needle (e.g., as shown in FIG. 9) continues through to its distal tip with no bend or repositioning of the leading cutting edge.

Figure 10:
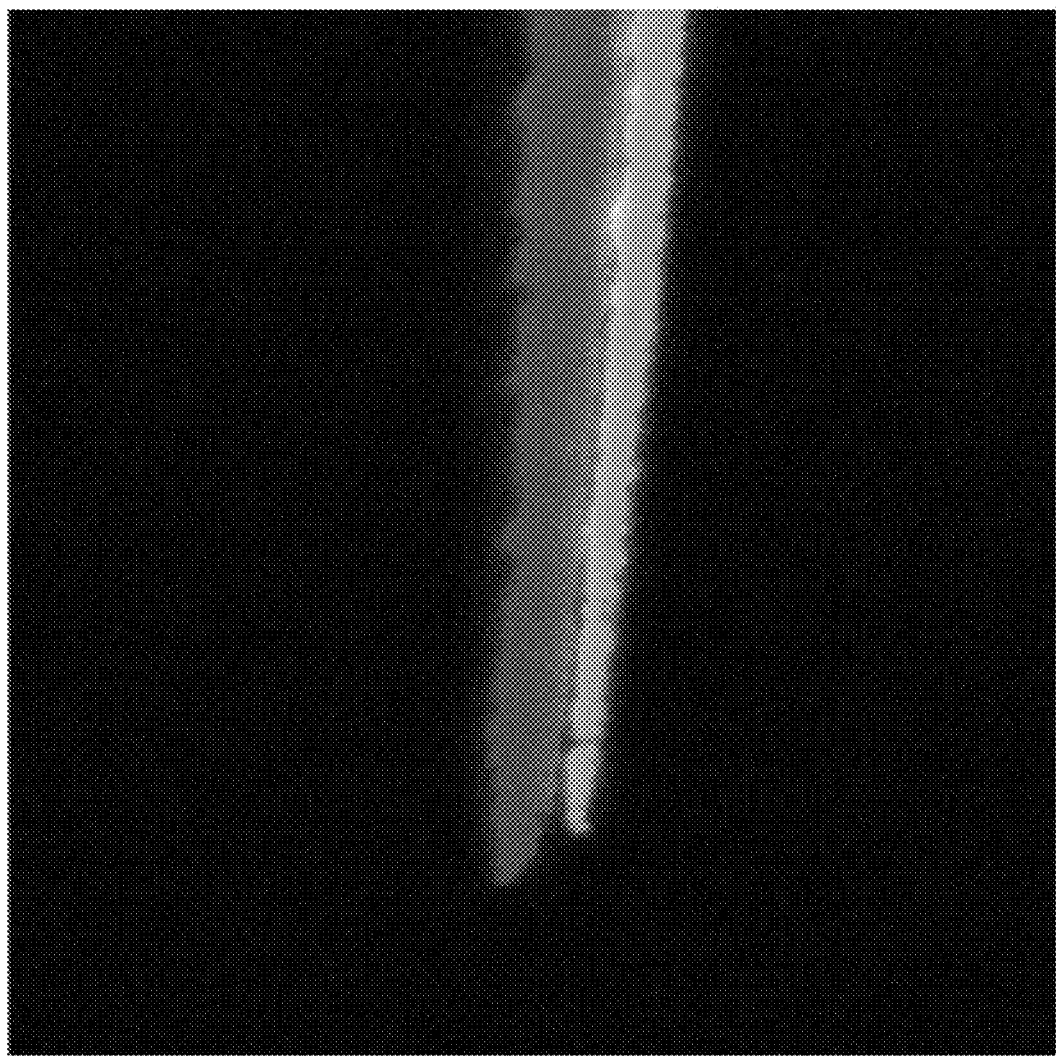
FIG. 10 is a cross-sectional view of a conventional needle track (on the left) next to a track made by a needle with blunt contours (on the right)
Figure 11:
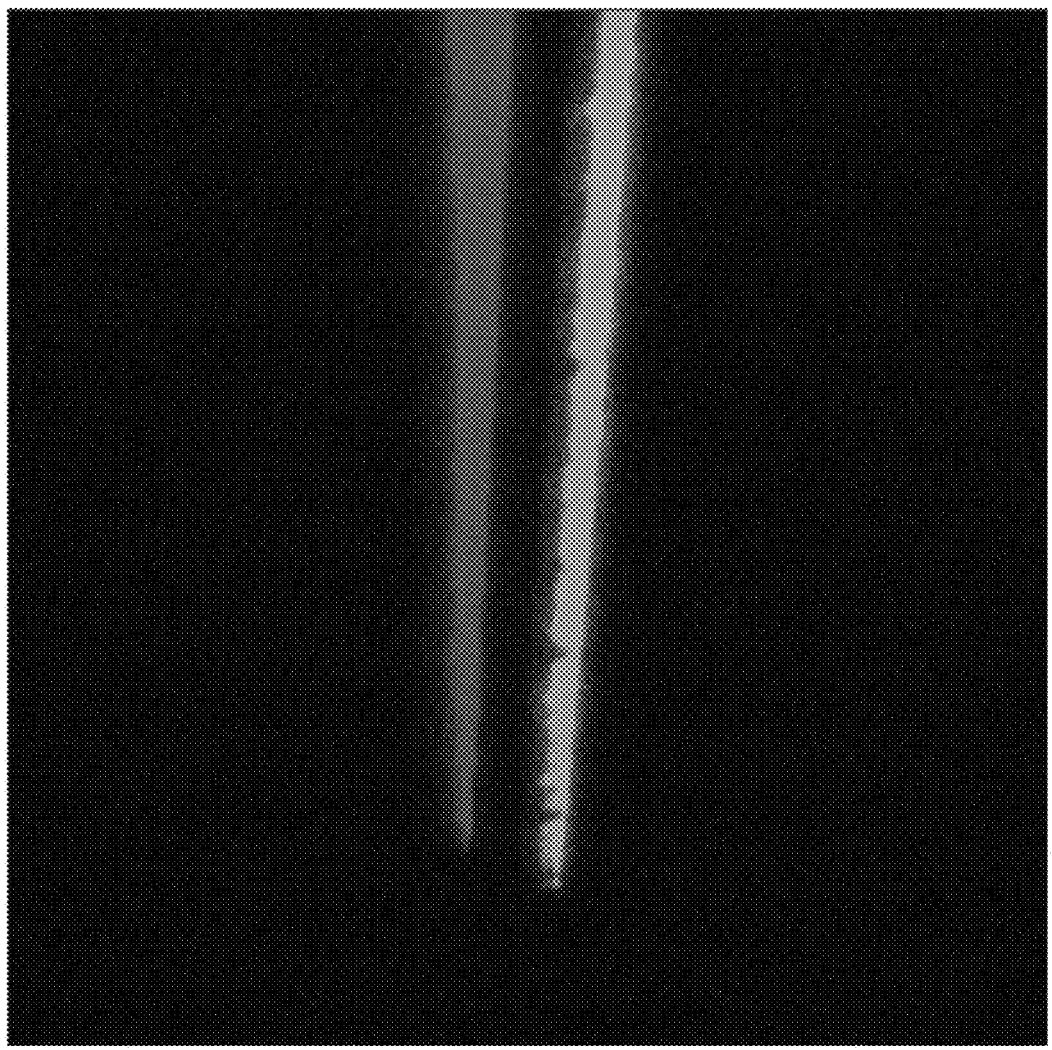
FIG. 11 is another cross-sectional view of a conventional needle track (on the left) next to a track made by a needle with blunt contours (on the right)

The needles were inserted into approximately 0.020 inch TPE material at 1 inch/minute using an INSTRON materials testing machine. The needle cuts were measured using a Keyence microscope. Notably, the conventional needle made a triangular shaped opening at the surface of the TPE while the (exemplary) needle made a slit. Further qualitatively, FIG. 10 shows the conventional needle track on the left which is larger in cross-section than the needle track on the right. FIG. 11 again illustrates how one disclosed needle design that balances the blunt contours 16 with the cutting edge 14 and reduces the degree of tissue trauma caused along the track (on the right) by needle insertion in comparison to the conventional needle track (on the left).

FIG. 12 shows a table comparing the wound diameter (microns), wound length (microns) and wound volume (square microns) created by the needle insertion for the best and worst performing measurements on 5 samples of each needle. The conventional needles left entry wounds having larger diameters at the surface of the TPE—for example 47.5 and 81 micrometers compared 34.3 and 45 micrometers respectively. Wound volumes were measured by creating 3D models from the images. The wound volumes in these examples were reduced about 49% and 69% using a needle 10 with a 17 degree bend angle and 7 degree primary bevel and 12.4 degree secondary bevel. Wound volume improvements could also be less depending upon the balance of blunt to cutting areas, such as a 15% or 35% reduction.

Early animal tests were performed using live porcine specimens with conventional needles next to needles with 10 degree bend angles and other design characteristics disclosed herein. Sixty percent of the glucose measurements with the needle showed some reduction in dip and recover characteristics compared to the conventional needle adjacent on the same animal.

Figure 5:
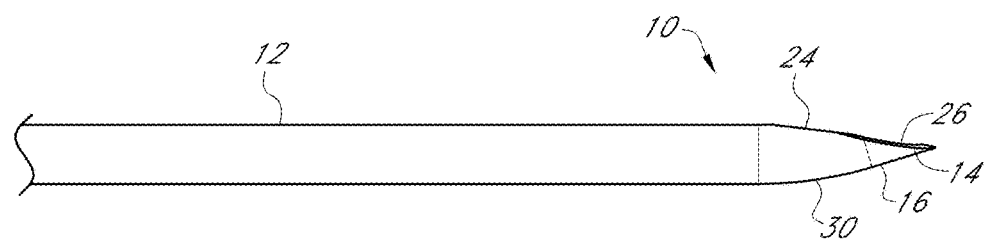
FIG. 5 shows an elevation view of the tubing of FIG. 4 with a secondary bevel formed thereon.

FIGS. 3-5 illustrate in part how the needle 10 is manufactured. Stock tubing is first bent to a predetermined angle (e.g., about 10 or 17 degrees) to form the bend 30 in wall structure 12. The primary bevel 24 is then ground or machined to the first desired angle. Then, the secondary bevels 26 are ground to the second desired angle. Non-cutting edges are blasted with material to round them out and remove burrs. The cutting edges 14, if necessary, are either present from the grinding or generated by further sharpening on the axially directed bevel edges.

Figure 16:
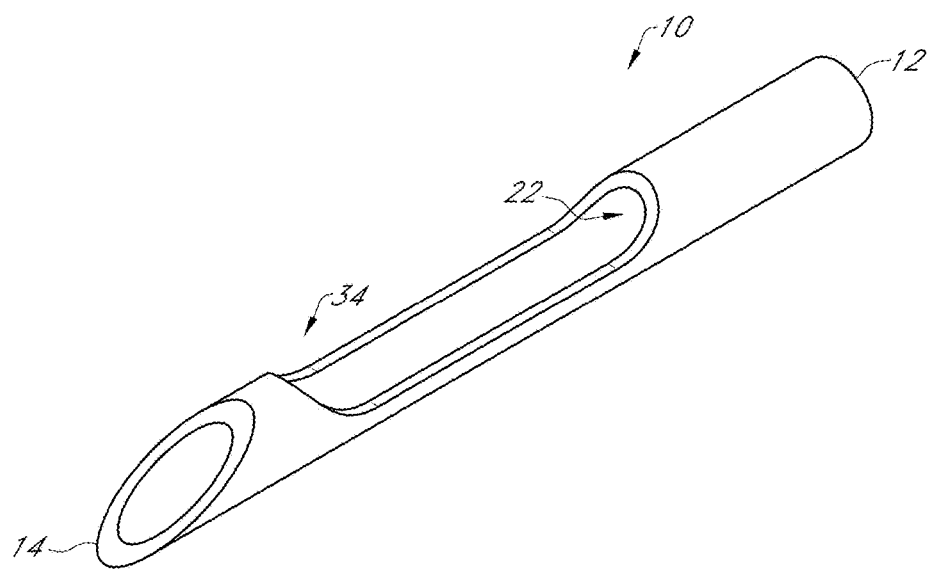
FIG. 16 is a perspective view of a needle of another embodiment wherein the needle has a slot.
Figure 17:
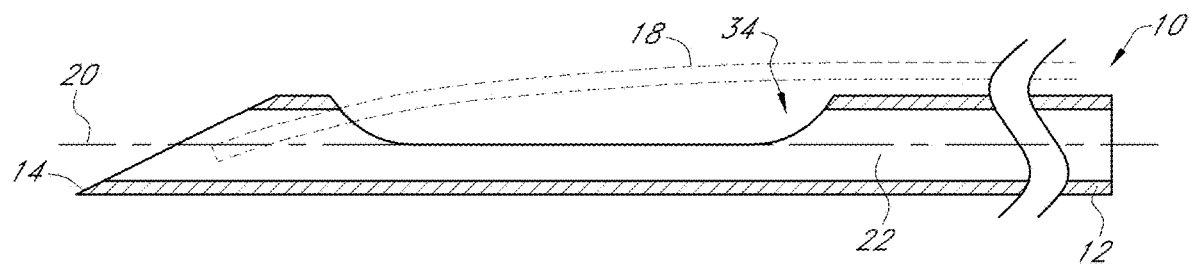
FIG. 17 is cross-sectional view of the needle of FIG. 16.

Referring now to FIGS. 16-17, the needle 10 may be designed with slot 34 (or slots). These slots may facilitate delivery or removal of the sensor 18, or aid in reducing wound trauma. FIGS. 16 and 17, for example, illustrate slot 34 formed as a window near the distal end of the wall structure 12 of the needle 10. The slot 34 is formed by cutting a portion (e.g., about half of the circumference of the tubular wall structure) away and having ramped or rounded (radius about 0.5 to about 1 inches) walls near the proximal and distal ends for a smooth transition. In the particular embodiment shown, the distal edge of the slot 34 is about 0.8 mm from the end of the wall structure 12 beginning at the primary bevel 24. The slot 34 is about 3 mm long. Advantageously, the sensor (shown in dashed lines) can be inserted through the slot 34 into the distal-most, closed section of the wall structure 12, allowing it to be more easily freed for delivery. It is contemplated that the dimensions corresponding to the embodiment illustrated in FIGS. 16 and 17 can be different depending at least in part on the dimensions of the sensor to be inserted.

Figure 18:
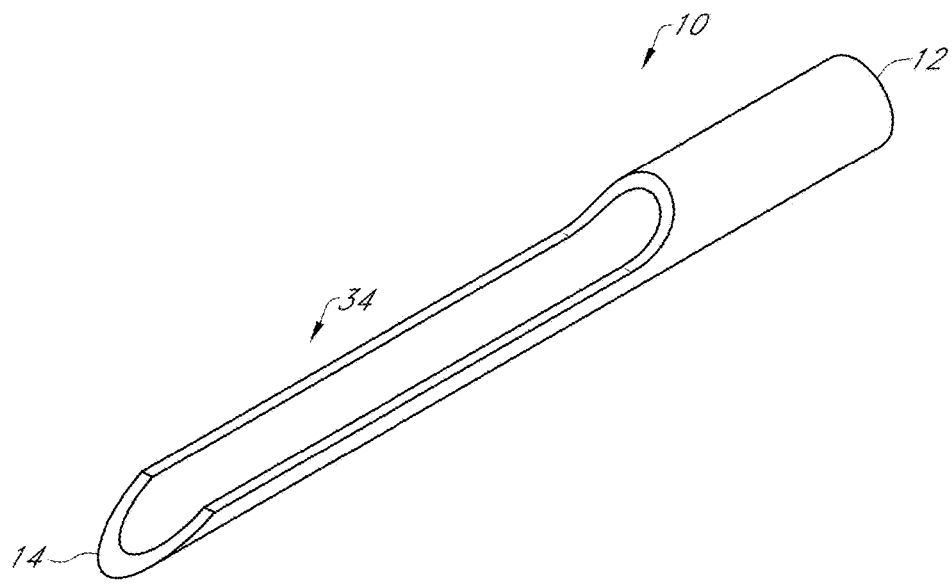
FIG. 18 is a perspective view of another needle with a slot extending through the distal end of the needle.
Figure 19:
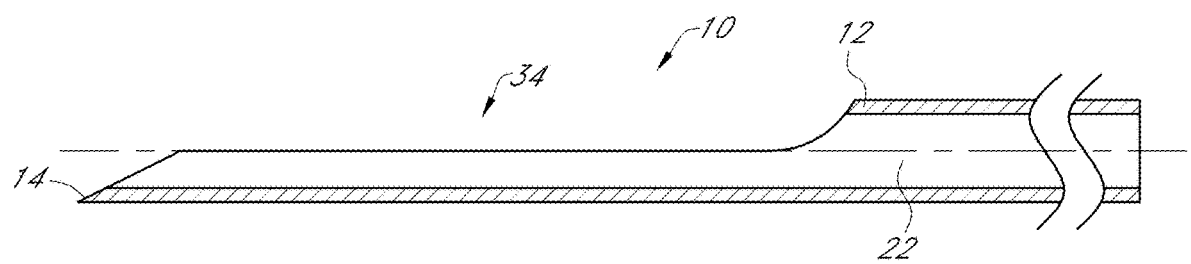
FIG. 19 is a cross-sectional view of the needle of FIG. 18.

FIGS. 18-19 illustrate a needle with a slot 34 that extends to the distal end of the needle 10. In one embodiment, the proximal closed portion of the needle wall structure 12 is about 8 mm and the slot extends along 6 mm of the end of the wall structure. Viewed along the central axis, the slot 34 forms a C-shape at the distal end of the needle.

Sensor delivery systems that employ a needle without a slot are typically unable to deliver a pre-connected sensor (i.e., a sensor connected to sensor electronics prior to sensor insertion). With these systems, electrical connection between the sensor and the sensor electronics occurs after the sensor has been inserted and often after the needle has been retracted. In some embodiments, such as the embodiment illustrated in FIGS. 18 and 19, a slot 34 facilitates removal of the needle from a pre-connected sensor which may be designed to connect to sensor electronics through an electrical wire that extends through the slot prior to and during sensor insertion. After sensor insertion, the slot 34 allows for removal of the needle from the sensor 18 without disturbing the electrical connection which was already established prior to insertion.

In short, the C-shape or V-shape or other shape formed by a slot 34 extending through the distal end of the needle 10 may provide for delivery of pre-connected sensors 18. The wires from the sensor can extend through the slot 34 while the rest of the sensor is held within the opening 22. More than one slot could be used, such as for several electrical connectors. In addition, the slots may vary in size, shape and positioning depending upon the desired use and/or reduction of invasiveness.

The windows and slots may be combined with the bend and other characteristics of the needles illustrated in FIGS. 1-8.

An example of another slotted needle implementation is shown in FIGS. 21-24. In particular, as shown by FIG. 24, the needle 10 at its straight, proximal portion has a U-shaped cross-section. The wall structure 12 includes, in this cross-section, a semi-circular bottom portion and straight arm portions extending up from the semi-circular bottom to form the U. The spacing between the arm portions forms a slot 34. The slot 34 is preferably sized to allow removal of the sensor 18. In other words, the slot is wider than the width of the sensor 18. The bend 30 in this implementation has a 17 degree angle, the primary bevel 24 is 7 degrees and the secondary bevel is 12 degrees. However, the bends and bevels can vary as described elsewhere herein.

Figure 14:
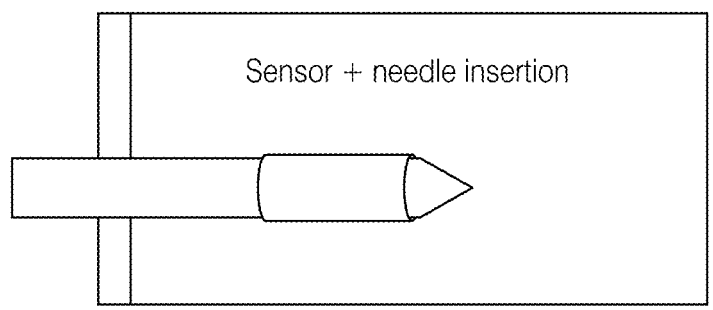
FIG. 14 shows insertion of the coaxial sensor of FIG. 13 on a pencil point needle.
Figure 15:
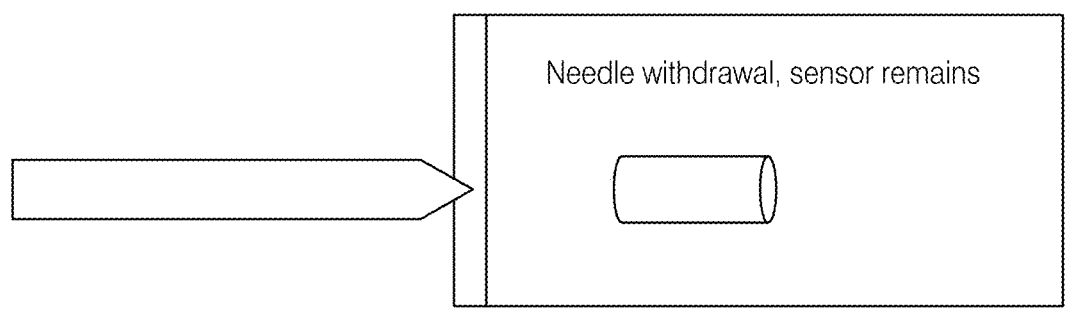
FIG. 15 shows removal of the pencil point needle from the coaxial sensor of FIG. 13.

FIGS. 14-15 illustrate another embodiment of the needle 10 for delivering a coaxial sensor 18. The sensor 18 is a hollow fiber sensor mounted on the outside of a conical tipped (pencil point) needle. That needle is used to pierce the dermal and subdermal layers, carrying the sensor with it, as shown in FIG. 14. The needle 10 is then withdrawn, leaving the sensor 18 behind in the patient. The conical tip needle has a large amount of dilation contour and therefore reduces wound trauma and the incidence of dip and recover.

Figure 13:
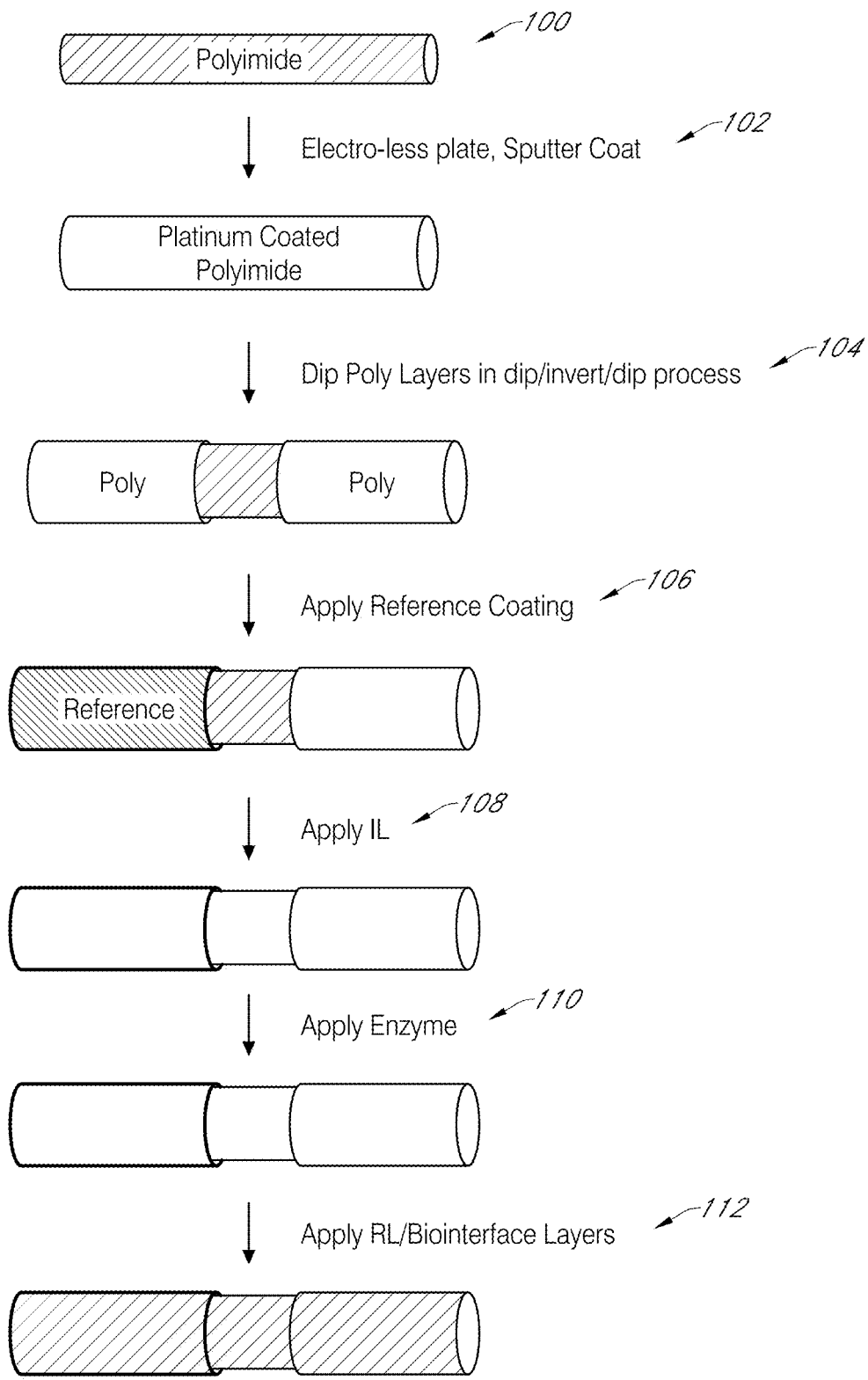
FIG. 13 is a diagram of a process for creating a coaxial sensor.

FIG. 13 illustrates one embodiment of the manufacturing of the sensor, starting with a polyimide hollow fiber (step 100). Platinum or other conductive metal is deposited on the hollow fibers, such as via sputter coating, thermal evaporation, electroless plating, etc. (step 102). A polymeric layer is applied using a dip coating process via dip invert and dip method (step 104). A reference coating is applied to one end (step 106). Then the whole assembly is coated in an interference layer (step 108), an enzyme layer is applied (step 110), and various RL/biointerface layers are applied (step 112).

The hollow fiber need not be retained; it can be removed from the sensor after forming. Also, rather than a full cylinder, the sensor 18 could be only half a cylinder to make it more flexible for tissue compliance. Use of the polymer based structural support for the sensor 18 allows its mechanical properties to be tuned. For long term tissue integration, the sensor 18 can have its stiffness (Young's modulus) matched to that of the surrounding tissue. Also, the sensor 18 structure can be designed to collapse on itself after needle withdrawal to increase flexibility. It should be understood that other variations of sensors may be inserted with the needles described herein, including the sensors described in U.S. patent application Ser. No. 12/829,296, filed Jul. 1, 2010, issued as U.S. Pat. No. 8,828,201 and in U.S. patent application Ser. No. 14/058,154, filed Oct. 18, 2013, issued as U.S. Pat. No. 8,954,128, both owned by the assignee of the present application and herein incorporated by reference in their entireties.

Another needle may accomplish the cutting and blunt dissection phases through uncoupling of the cutting and blunt dissection structures. The needle includes a cutting surface that is orthogonal to the axial direction of the needle.

For example, the cutting surface may be shaped like the helical cutting surface on a drill bit or hand tap. Otherwise, in the linear direction the needle is relatively blunt at its tip—such as a rounded pencil point tip. This needle while moving in the linear direction (in and out of the skin) will not present the cutting surface—it bluntly dilates the tissue. However, if the needle is rotating on its longitudinal axis, the cutting surface is presented and a hole is created. Thus, this "drill bit" style needle can be deployed using a mechanical system similar to an automatic or hand drill. The mechanical system will rotate and longitudinally translate the needle into the skin to puncture the skin surface into the subcutaneous space of predefined distance. After this initial skin puncture, the needle will then be pushed longitudinally deeper into the subcutaneous space without providing cutting action.

Figure 37:
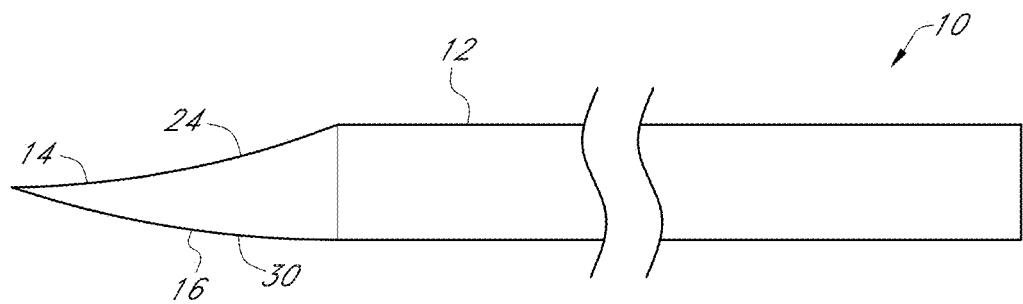
FIGS. 37-38 show a single bevel embodiment of a needle.
Figure 38:
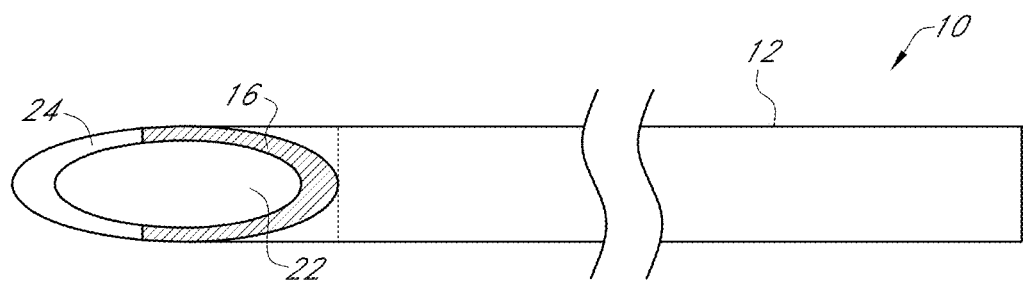

FIGS. 37 and 38 show another embodiment of the needle 10. The needle 10 includes a single primary bevel 24 having a 13 degree angle for the bend 30 from the lower horizontal wall line of the wall structure 12. The point is elevated 0.152 (plus/minus 0.051) mm from the bottom wall line of the wall structure. The needle 10 has an inner diameter of 0.343 (plus 0.025/minus 0.013) mm and an outer diameter of 0.457 (plus 0.025/minus 0.013) mm. The primary bevel has a gentle curvature extending from its tip to the proximal edge. A bevel length of 1.270 (plus/minus 0.152) mm is shown. Shown in cross-hatch is a bead blasted (for burr removal and anti-coring) proximal length of 0.762 (plus/minus 0.152) mm. Advantageously, reducing the bend angle from 17 to 13 degrees reduced the chances of sensor damage during deployment.

Figure 39:
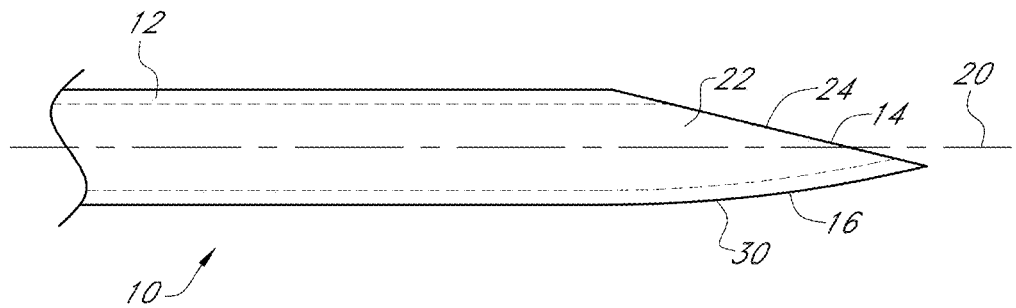
FIG. 39 shows another single bevel embodiment of a needle with a 13 degree bend angle.

FIG. 39 shows another embodiment of the single-bevel needle 10 with a 13 degree bend 30, but with no gentle curve in its bevel 24. Instead, the primary bevel is straight and at about a 13.5 degree angle with respect to the top outer edge of the wall structure 12.

Figure 40:
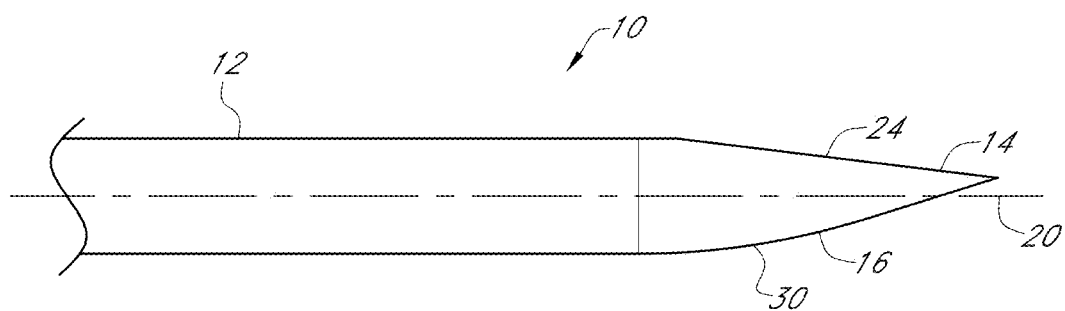
FIG. 40 shows another single bevel embodiment of a needle with a 17 degree bend angle.
Figure 45:
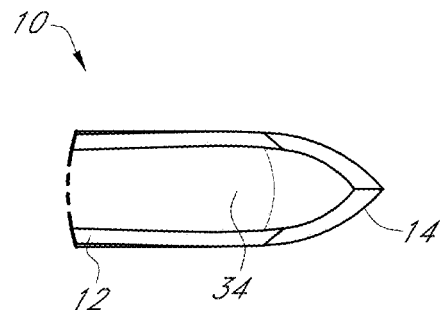
Figure 46:
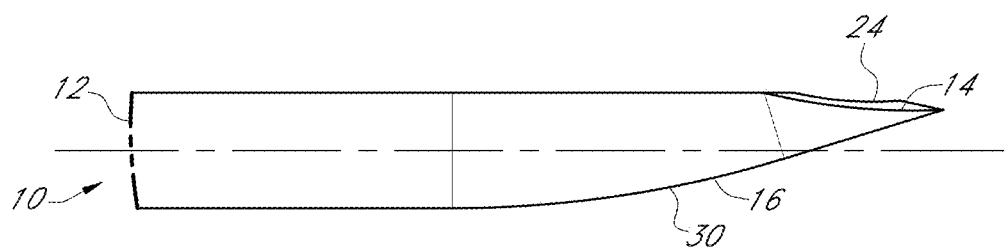

FIG. 40 shows another embodiment of the needle 10 with a single bevel 24, including a 17 degree bend angle and a 7 degree bevel angle. The point is elevated 0.012 inches from the bottom edge of the wall structure 12.

FIGS. 41-44 show a U-shaped needle 10 including a top slot 34 defined between arms of the U-shape. The bend 30 has a 13 degree angle and the single primary bevel 24 has an angle of 7 degrees. The point is elevated 0.011 inches from the bottom edge of the wall structure 12. The needle 10 has a diameter of 0.013 (plus/minus 0.004) inches and the height of the walls (from the bottom curved edge of the "U") is 0.017 (plus/minus 0.004) inches. The slot is 0.013 (plus/minus 0.003) inches wide between the top inner edges of the arms. The needle 10 has a wall thickness of 0.0025 (plus/minus 0.0004) inches. The bevel has a length of 0.05 inches.

FIGS. 45-49 show tack-slotted needle 10 having slot 34 extending only partially (about 0.60 inches) along a distal length of the wall structure 12. The needle 10 includes a 17 degree bend 30 and a 12 degree primary bevel 24. The primary bevel 24 has two primary bevels 24 that are angled away from each other. The use of two angled primary bevels 24 creates a slight scalloped appearance when viewed in cross-section, toward the distal tip of the needle 10, as shown in FIG. 49. The distal length of the needle 10 starting at the bend is 0.05 inches and less than the length of the primary bevel 24. The slot 34 is formed of an axially extending resection of a top portion of the circular wall structure opposite the bend 30. FIG. 49 shows the cross-section of the needle 10 having a C-shape with the arms of the C having a height of about 0.012 inches, about 0.003 inches higher than the center axis of the needle proximal the bend.

In another embodiment, the needle (or needles) 10 described herein can be inserted with an automatic inserter, such as the automatic inserters (applicators) and associated structure disclosed in U.S. Patent Application Ser. No. 62/244,520 filed Oct. 21, 2015 entitled TRANSCUTANEOUS ANALYTE SENSORS, APPLICATORS THEREFOR, AND ASSOCIATED METHODS and Ser. No. 13/826,372 filed Mar. 14, 2013 entitled TRANSCUTANEOUS ANALYTE SENSORS, APPLICATORS THEREFOR, AND ASSOCIATED METHODS both of which are incorporated herein, by reference, in their entirety.

Figure 50:
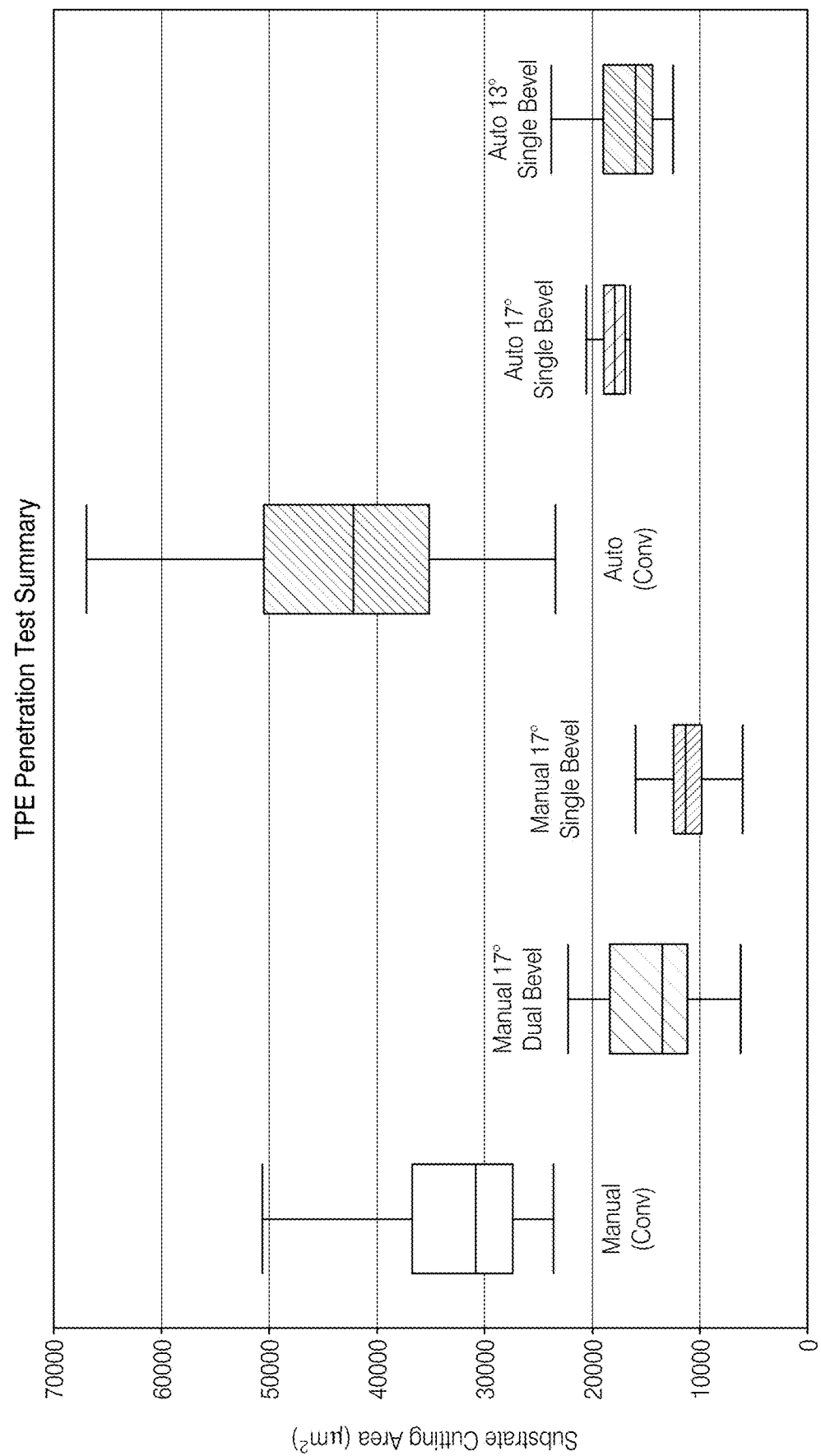
FIG. 50 graphically depicts cut area test results for needles.

Tests were conducted to determine the amount of substrate cut during penetration of selective needles compared to conventional needles. The method including deploying the sensor 18 into ¼ inch thick thermoplastic elastomer. Then, the sensor was removed right after its deployment. The area of the cut at the surface was then measured using a KEYENCE software and measurement system. FIG. 50 shows the comparative results, left-to-right, of the amount of area cut on the surface of the substrate for A) manual insertion of a conventional (CONV) needle, 17 degree dual bevel needle (FIG. 1), and 17 degree single bevel needle (FIG. 39); and B) auto-insertion of a conventional (CONV) needle, 17 degree single bevel needle (FIG. 40) and 13 degree single bevel needle (FIG. 39).

FIG. 51 shows a table of statistical results of testing of the six needles graphically illustrated in FIG. 50. Notably, mean area of cut for manual insertion dropped more than 50% from 31,872 square micrometers for the conventional needle to 14,564 square micrometers for the dual bevel needle and 11,459 for the 17 degree single bevel needle. The mean area of cut for auto insertion also dropped more than 50% from 43,103 square micrometers for the conventional needle to 17,588 square micrometers for the 17 degree single bevel needle and 16,846 square micrometers for the 13 degree single bevel needle.

Figure 52:
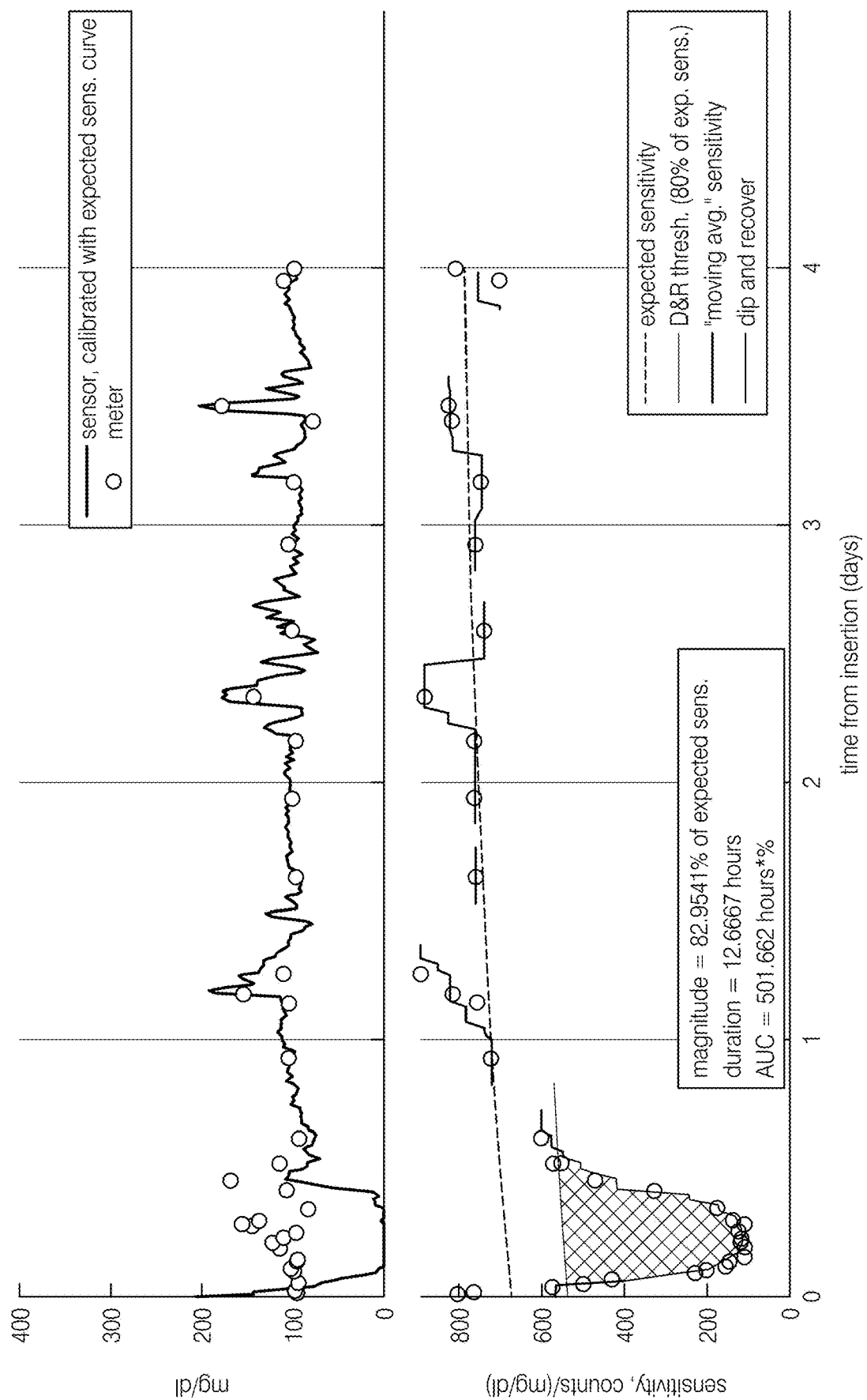
FIG. 52 graphically depicts a part of a process of testing for dip and recover behavior of a sensor delivered by needles.

The ability of the single-bevel needles to improve the incidence of dip and recover was assessed. FIG. 52 shows the testing methodology for a sample subject. Sensor data measuring mg/dl of blood glucose content was collected (continuous line, top graph) from the sensor deployed by conventional and needles and plotted against meter data over time. Then, the mg/dl measurements were adjusted with a moving average and fit to an expected sensitivity curve. A threshold for dip and recover of 80% of expected sensitivity was applied and the dip below and return to that threshold was defined as the duration and magnitude of the dip and recover. (A 17% drift from stable sensitivity 48-120 hours from insertion of the sensor 18 was assumed)

Figure 53:
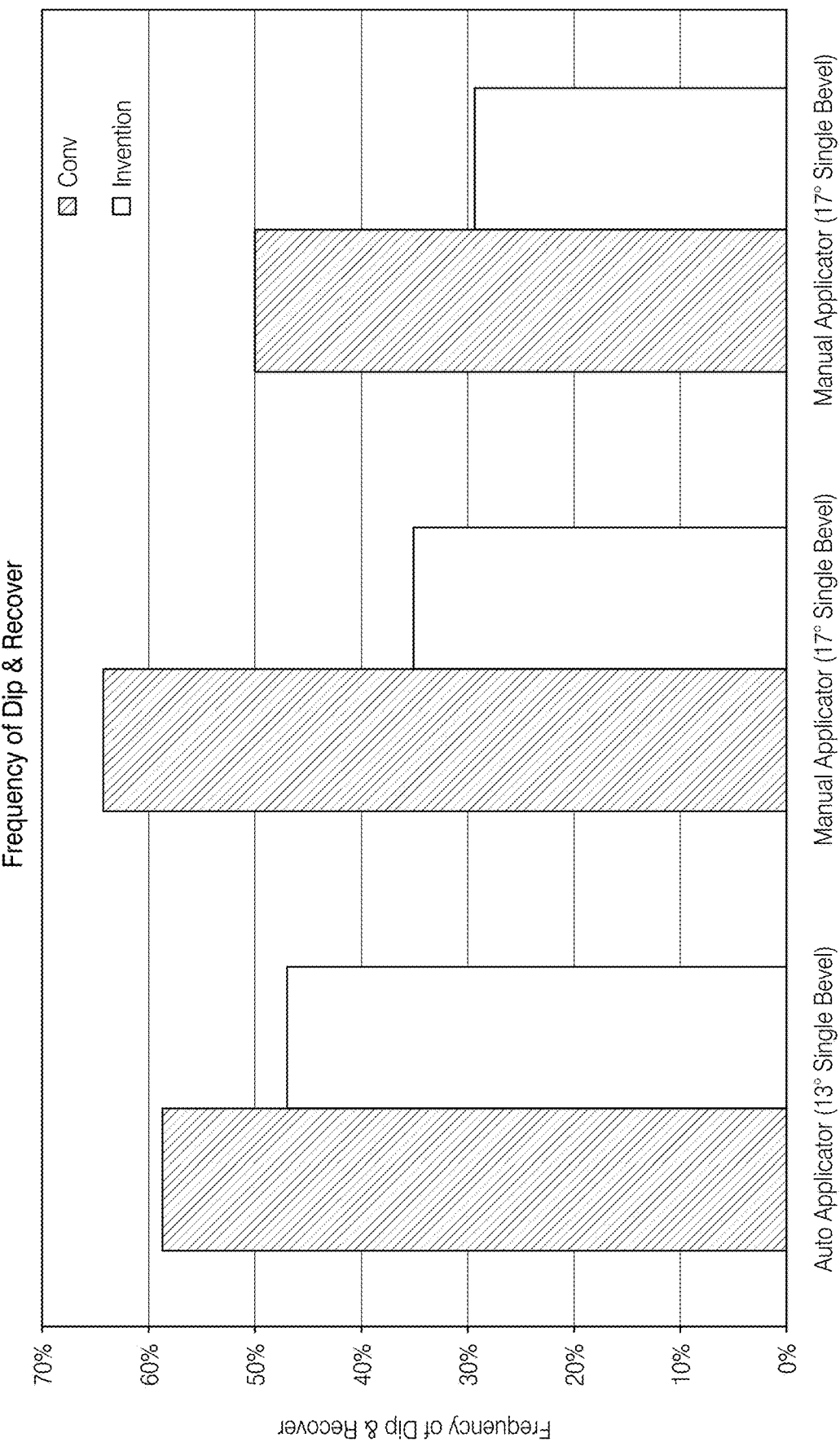
FIG. 53 graphically depicts dip and recover test results for conventional needles and needles of the embodiments.

Three clinical tests (sample size greater than 30) were conducted comparing conventional needles to various needles. As shown by FIG. 53, dip and recover was reduced from 64.7% to 35.3% for manual application of the dual bevel needle 10 (shown in FIG. 1) having a 17 degree bend. Dip and recover was reduced from 50% to 29.4% for manual application of the single bevel needle 10 (shown in FIG. 39) having a 17 degree bend. Dip and recover was reduced from 58.8% to 47.1% for insertion by auto applicator of the single bevel needle 10 (shown in FIG. 40) having a 13 degree bend.

Figure 54:
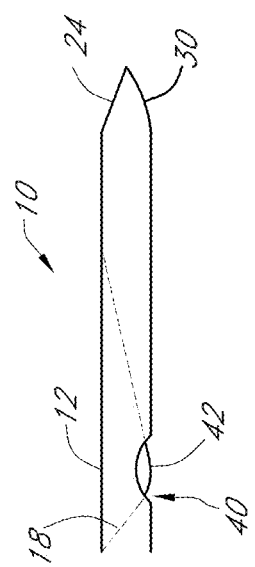
FIG. 54 shows another needle including a proximal slot to receive a kink of a sensor.

FIG. 54 shows another embodiment of the needle 10 wherein the wall structure defines a proximal slot 40. The proximal slot is scalloped into a portion of the needle on the side of the needle 10 having the point. The sensor 18 includes a kink 42 configured to seat into the proximal slot

40 so as to maintain the orientation of the sensor. In particular, the proximal portion of the sensor dips down into—and optionally somewhat extending out of—the proximal slot 40, reverses direction and continues distally into alignment with the needle central opening 22, opposite the proximal slot. Advantages of the proximal slot 40 include holding the sensor 18 in a specified position until a pushrod moves it out of position. Also, needle assembly would be facilitated by holding the sensor 18 in a desired or predictable position. Another advantage is the bend 30 of the needle 10 can be cleared by biasing the sensor 18's distal end to the opposite side of the wall structure 12. The sensor 18 would be less likely to run into the bend in the central opening 22 during deployment.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A needle for delivering a sensor through an outer skin layer and into a sensor depth, the needle comprising:
    a wall structure having a central axis, an outer surface, an interior surface, a tip, and at least one cross dimension and defining at least one inner dimension sized to contain the sensor for delivery, wherein the at least one inner dimension is configured to receive a bent portion of the sensor, wherein the interior surface of the wall structure comprises a lubricant coating, wherein the wall structure defines a first beveled edge and a second beveled edge;
    at least one cutting edge on the wall structure configured to pierce the outer skin layer, wherein the at least one cutting edge is formed only on the second beveled edge and not the first beveled edge, and wherein the at least one cutting edge formed on the second beveled edge is less than 50% of a combined beveled edge of the first beveled edge and the second beveled edge; and
    a bend of the wall structure forming at least one blunt contour on the wall structure, the bend extending through the central axis and positioning the tip between the central axis and an axis of the interior surface of the wall structure, the blunt contour configured to bluntly dissect tissue as the wall structure advances into the sensor depth;
    wherein the blunt contour, viewed along the central axis of the wall structure, occupies more than 50% of the cross dimension of the wall structure;
    wherein a ratio of a blunt surface area of the wall structure to a cutting surface area of the wall structure viewed along the central axis is no greater than 2.74; and
    wherein the wall structure is configured for removal from the outer skin layer to leave the sensor at the sensor depth.

2. The needle of claim 1, wherein the blunt contour is more than 60% of the cross dimension of the wall structure.

3. The needle of claim 1, wherein the at least one cutting edge, when viewed along the central axis of the wall structure, is spaced closer to the central axis than an adjacent outer edge of the blunt contour.

4. The needle of claim 1, wherein the blunt contour is at least ⅔ of an area centered on the central axis and circumscribing an outer edge of the blunt contour.

5. The needle of claim 4, wherein the area is a circular area and has a diameter matching a diameter of the wall structure.

6. The needle of claim 1, wherein the at least one cutting edge is formed on less than 40% of the combined beveled edge.

7. The needle of claim 1, wherein the blunt contour is sufficiently large in proportion to the cutting edge to reduce wound volume by at least 15%.

8. The needle of claim 1, wherein at least one of the first beveled edge or the second beveled edge is angled at least 7 degrees.

9. The needle of claim 8, wherein at least one of the first beveled edge or the second beveled edge is angled at least 10 degrees.

10. The needle of claim 1, wherein the includes a bend is positioned proximal to the cutting edge.

11. The needle of claim 10, wherein the bend is subjacent to at least one of the at least one cutting edge, the first beveled edge, or the second beveled edge.

12. The needle of claim 11, wherein the bend is at least 13 degrees.

13. The needle of claim 1, wherein the wall structure defines a longitudinal slit connected in communication with the inner dimension.

14. The needle of claim 13, wherein the wall structure defines an elongate opening and the inner dimension is a diameter of the opening and wherein the longitudinal slit is in communication with the elongate opening.

15. The needle of claim 14, wherein the elongate opening and the longitudinal slit extend entirely through a distal edge of the wall structure to form a cross sectional C-shape.

16. The needle of claim 1, wherein the first beveled edge is proximal to the second beveled edge, wherein the first beveled edge has an angle less than the second beveled edge.

17. The needle of claim 1, wherein only a portion of the first beveled edge and the second beveled edge positioned within a circle centered on the central axis and circumscribed about a bottom edge of the wall structure is sharpened, and a portion of the first beveled edge and the second beveled edge positioned outside of the circle is rounded.

18. The needle of claim 17, wherein the circle has a same diameter as a diameter of the wall structure.

19. The needle of claim 1, wherein the bend extends towards an opposite side of the wall structure along the cross dimension of the wall structure and positions the tip no more than 65% across the cross dimension of the wall structure.

20. The needle of claim 1, wherein the bend has an angle of between 10 degrees and 20 degrees.

* * * * *